US012596090B2

(12) United States Patent
    Watanabe

(10) Patent No.: US 12,596,090 B2
(45) Date of Patent: Apr. 7, 2026

(54) GAS SENSOR

(71) Applicant: NGK INSULATORS, LTD., Nagoya (JP)

(72) Inventor: Yusuke Watanabe, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 295 days.

(21) Appl. No.: 18/333,801

(22) Filed: Jun. 13, 2023

(65) Prior Publication Data

US 2023/0408440 A1 Dec. 21, 2023

(30) Foreign Application Priority Data

Jun. 20, 2022 (JP) ................................. 2022-098980

(51) Int. Cl.
    *G01N 27/407* (2006.01)
    *G01N 27/406* (2006.01)
    *G01N 33/00* (2006.01)
(52) U.S. Cl.
    CPC ....... *G01N 27/407* (2013.01); *G01N 27/4065* (2013.01); *G01N 33/0027* (2013.01)
(58) Field of Classification Search
    CPC ............. G01N 27/407; G01N 27/4065; G01N 27/419; G01N 27/4175; G01N 27/4162;
    (Continued)

(56) References Cited

U.S. PATENT DOCUMENTS

2018/0284052 A1* 10/2018 Watanabe ............ G01N 27/419
2018/0284053 A1 10/2018 Watanabe et al.
(Continued)

FOREIGN PATENT DOCUMENTS

JP 5767158 B2 * 8/2015
JP 2018-173320 A 11/2018
(Continued)

OTHER PUBLICATIONS

Hattori et al., JP 5767158 B2, English translation, 2015 (Year: 2015).*
(Continued)

*Primary Examiner* — Shizhi Qian
(74) *Attorney, Agent, or Firm* — MATTINGLY & MALUR, PC

(57) ABSTRACT

A gas sensor includes a sensor element and a control unit thereof. The sensor element includes: a base part; a measurement-object gas flow cavity formed from one end part in a longitudinal direction of the base part; a pump cell including an intracavity electrode disposed in the measurement-object gas flow cavity; and a reference electrode disposed in a reference gas chamber formed inside the base part. The control unit includes: a driving control part; a storing part storing in advance, a standard correspondence relationship at a standard time at which a reference potential of the reference electrode is at a predetermined value; and a diagnosing part obtaining a diagnostic correspondence relationship, and comparing the obtained diagnostic correspondence relationship with the standard correspondence relationship to diagnose a deviation of a reference potential of the reference electrode at the diagnostic time from the predetermined value at the standard time.

12 Claims, 10 Drawing Sheets

(58) Field of Classification Search
CPC ............. G01N 27/4163; G01N 27/417; G01N
33/0027
See application file for complete search history.

(56) References Cited

U.S. PATENT DOCUMENTS

| | | | | |
|---|---|---|---|---|
| 2018/0284056 A1* | 10/2018 | Watanabe | .......... | G01N 27/4074 |
| 2018/0284057 A1* | 10/2018 | Watanabe | .......... | G01N 27/4071 |
| 2020/0064302 A1* | 2/2020 | Sekiya | ............... | G01N 27/4075 |
| 2020/0191744 A1* | 6/2020 | Watanabe | .......... | G01N 27/4072 |
| 2020/0200700 A1* | 6/2020 | Okamoto | ............. | G01N 27/409 |
| 2021/0109058 A1* | 4/2021 | Watanabe | .......... | G01N 33/0006 |
| 2021/0302354 A1 | 9/2021 | Watanabe et al. | | |

FOREIGN PATENT DOCUMENTS

| | | | |
|---|---|---|---|
| JP | 2020165815 A | * | 10/2020 |
| JP | 2021-156647 A | | 10/2021 |
| WO | 2020/004356 A1 | | 1/2020 |

OTHER PUBLICATIONS

Murakami et al., JP-2020165815-A, English translation, 2020 (Year: 2020).*

* cited by examiner

Measurement-
object gas

GAS SENSOR

CROSS-REFERENCE TO RELATED APPLICATION

The present application claims priority from Japanese application JP2022-098980, filed on Jun. 20, 2022, the contents of which is hereby incorporated by reference into this application.

BACKGROUND OF THE INVENTION

Technical Field of the Invention

The present invention relates to a gas sensor for detecting a target gas to be measured in a measurement-object gas.

Background Art

A gas sensor is used for detection or measurement of concentration of an objective gas component (oxygen $O_2$, nitrogen oxide NOx, ammonia $NH_3$, hydrocarbon HC, carbon dioxide $CO_2$, etc.) in a measurement-object gas, such as exhaust gas of automobile. For example, conventionally, the concentration of the objective gas component in exhaust gas of an automobile is measured, and an exhaust gas cleaning system mounted on the automobile is optimally controlled based on the measurement.

For example, JP 2021-156647 A discloses a sensor element including: an element body having, in its inside, a measurement-object gas flow part that introduces and flows a measurement-object gas and a reference gas chamber for storing a reference gas (e.g., air) as a reference for detecting the concentration of a specific gas in the measurement-object gas; and a reference electrode disposed in the reference gas chamber.

In such a gas sensor, the reference electrode is disposed so as to come into contact with a reference gas (e.g., air) as a reference for detecting the concentration of a specific gas in a measurement-object gas. For example, JP 2021-156647 A discloses a configuration in which the reference electrode is disposed in the reference gas chamber independently provided in the element body. Further, for example, JP 2018-173320 A discloses a configuration in which the reference electrode is covered by a porous reference gas introduction layer that introduces a reference gas and flows the reference gas to the reference electrode. Also, it is disclosed that a space where a reference gas is present and a sensor element chamber into which a measurement-object gas is introduced are separated by a sensor assembly and sealed so that the gases do not flow therebetween.

CITATION LIST

Patent Documents

Patent Document 1: JP 2021-156647 A
Patent Document 2: JP 2018-173320 A
Patent Document 3: WO 2020/004356 A1

SUMMARY OF THE INVENTION

Problems to be Solved by the Invention

In the case of such a gas sensor, when the oxygen concentration in a reference gas around the reference electrode changes for any reason, the detection accuracy of a target gas to be measured in a measurement-object gas may reduce.

When the oxygen concentration in a measurement-object gas is known, as described in, for example, JP 2021-156647 A, the oxygen concentration in a reference gas can be determined by a potential difference between the reference electrode and a measurement-object gas side electrode disposed in a portion of the sensor element exposed to the measurement-object gas, and if necessary can be adjusted. For example, when the measurement-object gas is exhaust gas from a car or the like, the measurement-object gas at the time of fuel cutoff is an air atmosphere, and therefore the oxygen concentration is known.

However, the oxygen concentration in a measurement-object gas usually changes by the minute, and therefore the oxygen concentration in the reference gas chamber cannot be determined by the above method during time other than a specific timing when the oxygen concentration is known, such as the time of fuel cutoff described above. Therefore, during time other than such a specific timing when the oxygen concentration is known, even when the oxygen concentration in a reference gas changes, such a change cannot be detected so that the detection accuracy of a target gas to be measured in a measurement-object gas may reduce.

In light of this, it is an object of the present invention to provide a gas sensor that can prevent a reduction in the detection accuracy of the target gas to be measured in the measurement-object gas to maintain high detection accuracy.

Means for Solving the Problems

The present inventor has studied to diagnose a deviation of the oxygen concentration in a reference gas and, if necessary, correct the deviation at any timing during the use of a gas sensor also in cases other than a case where the oxygen concentration in a measurement-object gas is known or irrespective of the oxygen concentration.

For example, WO 2020/004356 A1 discloses that a current is applied between a reference electrode and a measurement-object gas side electrode disposed in a portion exposed to a measurement-object gas to perform an oxygen pump-in control to pump oxygen into the surroundings of the reference electrode. Also, it is disclosed that in order to prevent a reduction in the detection accuracy of a target gas to be measured in a measurement-object gas, the concentration of a specific gas in the measurement-object gas is corrected based on a difference between a first base voltage across the reference electrode and the measurement-object gas side electrode when the oxygen pump-in control is not performed and a second base voltage across the reference electrode and the measurement-object gas side electrode when the oxygen pump-in control is performed. However, this correction is performed according to the amount of resistance change of the reference electrode due to deterioration with time, and is therefore not intended to be performed as a result of detection of a change in the oxygen concentration in a reference gas around the reference electrode.

The present inventor has intensively studied and as a result have found that by using a gas sensor having a configuration described below, a deviation of a reference potential of a reference electrode can be diagnosed. Further, the present inventor has found that by correcting the deviation of the reference potential of the reference electrode based on the result of the diagnosis, the deviation of the reference potential of the reference electrode, that is, a deviation of the oxygen concentration in a reference gas around the reference electrode can be corrected at any timing during the use of the gas sensor.

The present invention includes the following aspects.

(1) A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

a pump cell including: an intracavity electrode disposed in the measurement-object gas flow cavity; and an extracavity electrode disposed at a position different from the measurement-object gas flow cavity on the base part and corresponding to the intracavity electrode;

a reference gas chamber formed inside the base part, and being separated from the measurement-object gas flow cavity; and a reference electrode disposed in the reference gas chamber, and the control unit comprises:

a driving control part operating the pump cell to perform a normal control for detecting a target gas to be measured in a measurement-object gas;

a storing part storing in advance, a standard correspondence relationship of a voltage between the intracavity electrode and the reference electrode with a current flowing through the pump cell, at a standard time at which a reference potential of the reference electrode is at a predetermined value; and a diagnosing part obtaining a diagnostic correspondence relationship of a voltage between the intracavity electrode and the reference electrode with a current flowing through the pump cell at a diagnostic time at which a reference potential of the reference electrode is diagnosed, and comparing the obtained diagnostic correspondence relationship with the standard correspondence relationship stored in advance in the storing part to diagnose a deviation of a reference potential of the reference electrode at the diagnostic time from the predetermined value at the standard time.

(2) The gas sensor according to the above (1), wherein the storing part stores in advance, as the standard correspondence relationship, a standard voltage current curve of a voltage between the intracavity electrode and the reference electrode with a current flowing through the pump cell, at the standard time at which a reference potential of the reference electrode is at the predetermined value, and the diagnosing part sweeps a voltage applied to the pump cell within a predetermined range, obtains, as the diagnostic correspondence relationship, a diagnostic voltage current curve of a voltage between the intracavity electrode and the reference electrode with a current flowing through the pump cell, and compares the obtained diagnostic voltage current curve with the standard voltage current curve stored in advance in the storing part to diagnose a deviation of the reference potential of the reference electrode at the diagnostic time from the predetermined value at the standard time.

(3) The gas sensor according to the above (1) or (2), wherein the storing part stores in advance, as the standard correspondence relationship, a standard voltage between the intracavity electrode and the reference electrode at a time at which a current flowing through the pump cell is at a predetermined current value in a ohmic region in which a relationship of the voltage between the intracavity electrode and the reference electrode with the current flowing through the pump cell is linear, at the standard time at which a reference potential of the reference electrode is at the predetermined value, and the diagnosing part obtains, as the diagnostic correspondence relationship, a diagnostic voltage between the intracavity electrode and the reference electrode at the time at which a current is at the predetermined value, and compares the obtained diagnostic voltage with the standard voltage stored in advance in the storing part to diagnose a deviation of the reference potential of the reference electrode at the diagnostic time from the predetermined value at the standard time.

(4) The gas sensor according to the above (1) or (2), wherein the storing part stores in advance, as the standard correspondence relationship, a standard voltage between the intracavity electrode and the reference electrode at a time at which water ($H_2O$) starts to be decomposed in the intracavity electrode, at the standard time at which reference potential of the reference electrode is at the predetermined value, and the diagnosing part obtains, as the diagnostic correspondence relationship, a diagnostic voltage between the intracavity electrode and the reference electrode at the time at which water ($H_2O$) starts to be decomposed in the intracavity electrode, and compares the obtained diagnostic voltage with the standard voltage stored in advance in the storing part to diagnose a deviation of the reference potential of the reference electrode at the diagnostic time from the predetermined value at the standard time.

(5) The gas sensor according to the above (1) or (2), wherein the storing part stores in advance, as the standard correspondence relationship, a standard voltage between the intracavity electrode and the reference electrode at a time at which a current flowing through the pump cell reaches a limiting current, and the diagnosing part obtains, as the diagnostic correspondence relationship, a diagnostic voltage between the intracavity electrode and the reference electrode at the time at which a current flowing through the pump cell reaches a limiting current, and compares the obtained diagnostic voltage with the standard voltage stored in advance in the storing part to diagnose a deviation of the reference potential of the reference electrode at the diagnostic time from the predetermined value at the standard time.

(6) The gas sensor according to any one of the above (1) to (5), wherein the sensor element comprises:

a measurement pump cell including: an inner measurement electrode disposed in the measurement-object gas flow cavity; and an outer measurement electrode disposed at a position different from the measurement-object gas flow cavity on the base part and corresponding to the inner measurement electrode,

the driving control part applies a current to the measurement pump cell so that a voltage between the inner measurement electrode and the reference electrode is a target voltage to measure a concentration of a target gas to be measured in a measurement-object gas based on a value of the current in the normal control, and the diagnosing part further changes the target voltage in the normal control based on the deviation of the reference potential of the reference electrode at the diagnostic time from the predetermined value at the standard time to correct the deviation from the predetermined value.

(7) The gas sensor according to any one of the above (1) to (6), wherein the diagnosing part further pumps oxygen into the reference gas chamber or pumps out oxygen from the reference gas chamber based on the deviation of the reference potential of the reference electrode at the diagnostic time from the predetermined value at the standard time to correct the deviation from the predetermined value.

The gas sensor according to the above (6) or (7), wherein the diagnosing part changes the target voltage in the normal control and pumps oxygen into the reference gas chamber or pumps out oxygen from the reference gas chamber based on the deviation of the reference potential of the reference electrode at the diagnostic time from the predetermined value at the standard time to correct the deviation from the predetermined value.

(8) The gas sensor according to any one of the above (1) to (7), wherein the reference gas chamber is a space closed inside the base part.

(9) A control method of a gas sensor for detecting a target gas to be measured in a measurement-object gas, the gas sensor comprising a sensor element and a control unit for controlling the sensor element, wherein the sensor element comprises:
    a base part in an elongated plate shape, including an oxygen-ion-conductive solid electrolyte layer;
    a measurement-object gas flow cavity formed from one end part in a longitudinal direction of the base part;
    a pump cell including: an intracavity electrode disposed in the measurement-object gas flow cavity; and an extracavity electrode disposed at a position different from the measurement-object gas flow cavity on the base part and corresponding to the intracavity electrode;
    a reference gas chamber formed inside the base part, and being separated from the measurement-object gas flow cavity; and
    a reference electrode disposed in the reference gas chamber, and
the control unit comprises:
    a driving control part operating the pump cell to perform a normal control for detecting a target gas to be measured in a measurement-object gas;
    a storing part storing in advance, a standard correspondence relationship of a voltage between the intracavity electrode and the reference electrode with a current flowing through the pump cell, at a standard time at which a reference potential of the reference electrode is at a predetermined value; and
    a diagnosing part obtaining a diagnostic correspondence relationship of a voltage between the intracavity electrode and the reference electrode with a current flowing through the pump cell at a diagnostic time at which a reference potential of the reference electrode is diagnosed, and comparing the obtained diagnostic correspondence relationship with the standard correspondence relationship stored in advance in the storing part to diagnose a deviation of a reference potential of the reference electrode at the diagnostic time from the predetermined value at the standard time, and the control method comprising:
    a diagnosing step of obtaining a diagnostic correspondence relationship of a voltage between the intracavity electrode and the reference electrode with a current flowing through the pump cell by the diagnosing part, and comparing the obtained diagnostic correspondence relationship with the standard correspondence relationship stored in advance in the storing part to diagnose a deviation of a reference potential of the reference electrode at the diagnostic time from the predetermined value at the standard time.

Advantageous Effect of the Invention

The use of the gas sensor according to the present invention makes it possible to diagnose a deviation of a reference potential of the reference electrode at any timing during the use of the gas sensor also in cases other than a case where the oxygen concentration in a measurement-object gas is known or irrespective of the oxygen concentration. That is, it is possible to diagnose a deviation of the oxygen concentration in a reference gas around the reference electrode. Further, it is possible to correct a deviation of a reference potential of the reference electrode based on the result of the diagnosis. As a result, it is possible to increase the detection accuracy of a target gas to be measured in a measurement-object gas. It is possible to prevent a reduction in the detection accuracy of the target gas to be measured to maintain high detection accuracy.

BRIEF DESCRIPTION OF THE DRAWINGS

FIG. 2 is a vertical sectional schematic view in a longitudinal direction of a sensor element 101, which shows one example of the schematic configuration of the gas sensor 100.

FIG. 10 is a vertical sectional schematic view in a longitudinal direction of a sensor element 301 of a Variation.

MODES FOR CARRYING OUT OF THE INVENTION

A gas sensor of the present invention includes a sensor element and a control unit for controlling the sensor element.

The sensor element contained in the gas sensor of the present invention includes:

a base part in an elongated plate shape, including an oxygen-ion-conductive solid electrolyte layer;

a measurement-object gas flow cavity formed from one end part in a longitudinal direction of the base part;

a pump cell including: an intracavity electrode disposed in the measurement-object gas flow cavity; and an extra-cavity electrode disposed at a position different from the measurement-object gas flow cavity on the base part and corresponding to the intracavity electrode;

a reference gas chamber formed inside the base part, and being separated from the measurement-object gas flow cavity; and a reference electrode disposed in the reference gas chamber.

The control unit contained in the gas sensor of the present invention includes:

a driving control part operating the pump cell to perform a normal control for detecting a target gas to be measured in a measurement-object gas;

a storing part storing in advance, a standard correspondence relationship of a voltage between the intracavity electrode and the reference electrode with a current flowing through the pump cell, at a standard time at which a reference potential of the reference electrode is at a predetermined value; and a diagnosing part obtaining a diagnostic correspondence relationship of a voltage between the intracavity electrode and the reference electrode with a current flowing through the pump cell at a diagnostic time at which a reference potential of the reference electrode is diagnosed, and comparing the obtained diagnostic correspondence relationship with the standard correspondence relationship stored in advance in the storing part to diagnose a deviation of a reference potential of the reference electrode at the diagnostic time from the predetermined value at the standard time.

[Schematic Configuration of Gas Sensor]

Figure 1:
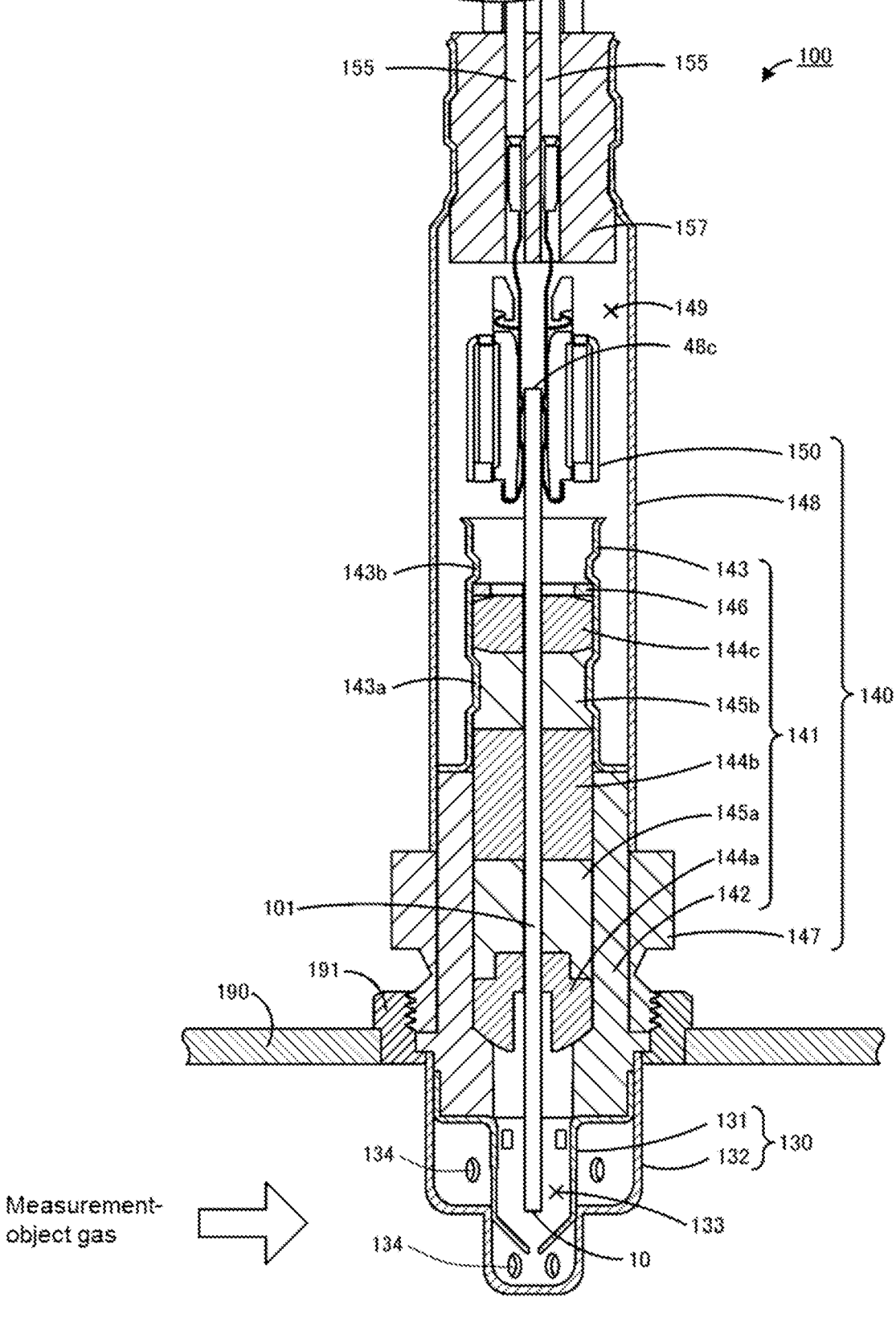
FIG. 1 is a vertical sectional view schematically showing one example of the schematic configuration of a gas sensor 100.
Figure 2:
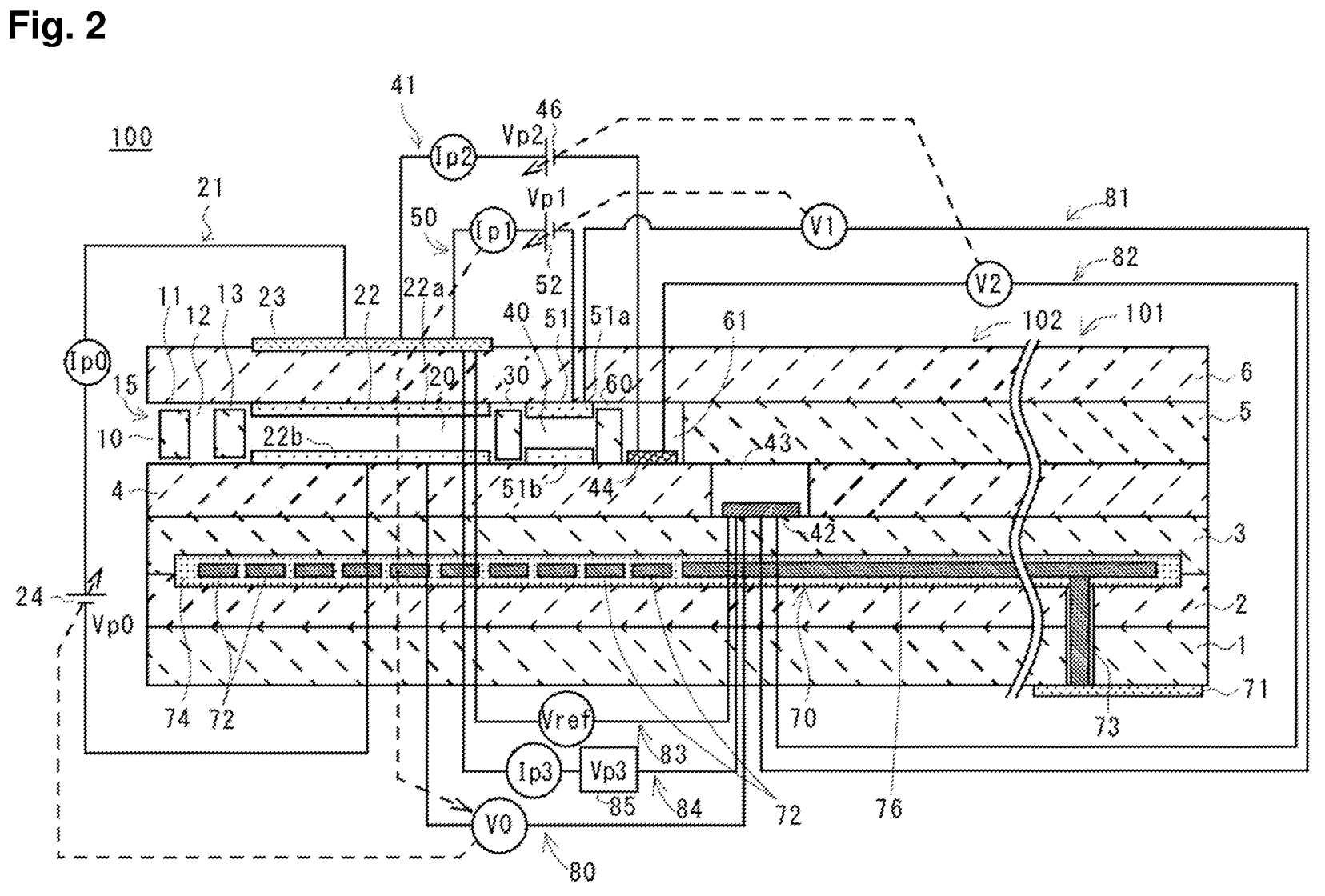
Figure 3:
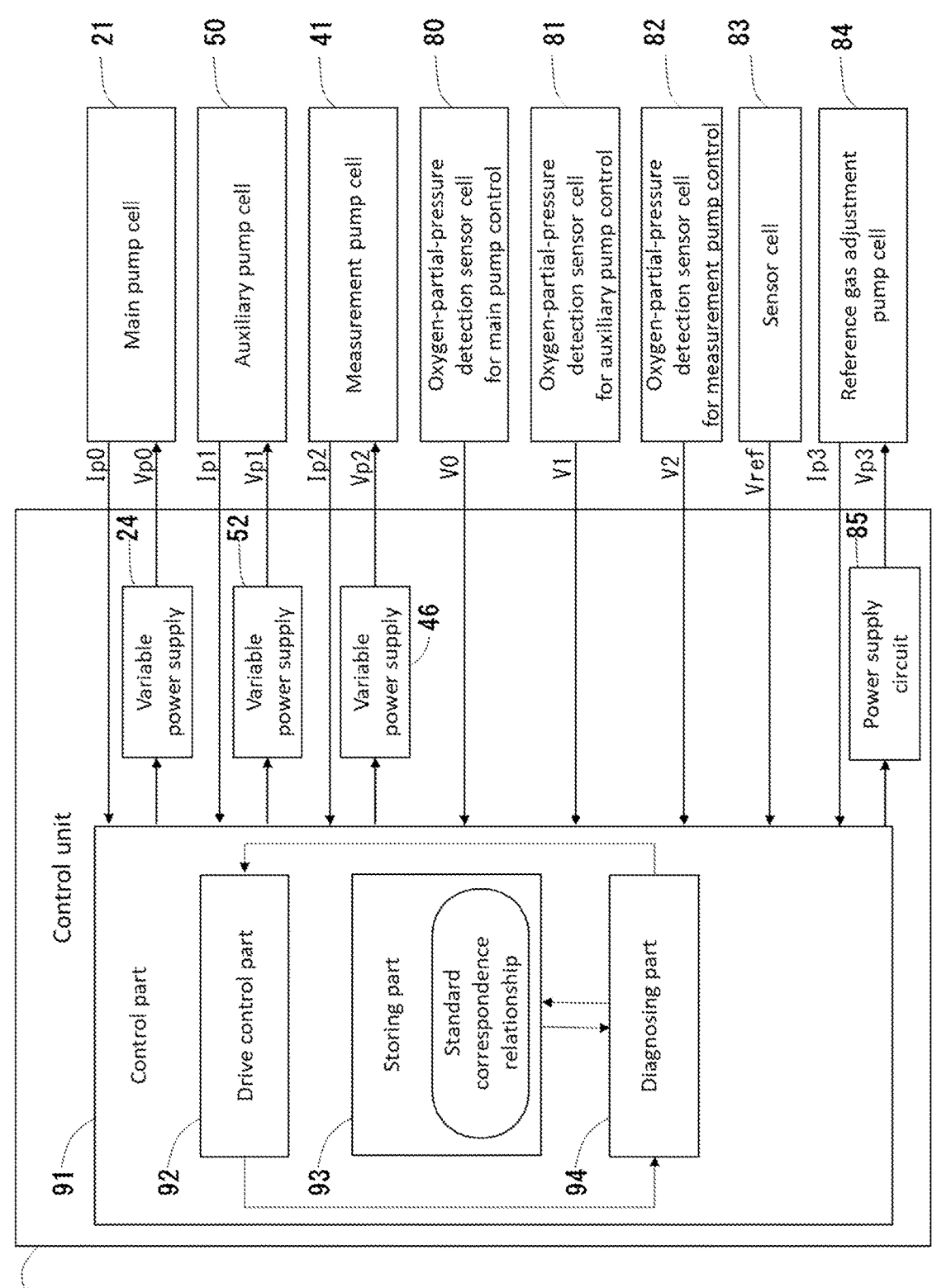
FIG. 3 is a block diagram showing electric connections between a control unit 90, and respective pump cells 21, 50, 41 and 84, and respective sensor cells 80, 81, 82, and 83 of the sensor element 101.

The gas sensor according to the present invention will be described below with reference to the drawings. FIG. 1 is a vertical sectional view schematically showing one example of the schematic configuration of a gas sensor 100 according to an embodiment of the present invention. FIG. 2 is a vertical sectional schematic view in a longitudinal direction of a sensor element 101, which shows one example of the schematic configuration of the gas sensor 100. FIG. 3 is a block diagram showing an example of electrical connections between a control unit 90 and the sensor element 101. Hereinafter, based on FIG. 2, the upper side and the lower side in FIG. 2 are respectively defined as top and bottom, and the left side and the right side in FIG. 2 are respectively defined as a front end side and a rear end side. The left side, right side, lower side, and upper side of FIG. 1 respectively correspond to top, bottom, front end side, and rear end side defined based on FIG. 2. It is noted that the structure of the gas sensor shown in FIG. 1 is well known and disclosed in, for example, JP 2021-156647 A, JP 2018-173320 A, and WO 2020/004356 A1.

As shown in FIG. 1, the gas sensor 100 includes a sensor element 101, a protection cover 130 to protect the front end side of the sensor element 101, and a sensor assembly 140 including a connector 150 electrically connected with the sensor element 101. As shown in FIG. 1, for example, this gas sensor 100 is attached to a pipe 190 such as an exhaust gas pipe of a vehicle and used to measure the concentration of a target gas to be measured, such as NOx, $NH_3$, or $O_2$, contained in exhaust gas as a measurement-object gas. In the present embodiment, the gas sensor 100 measures the concentration of NOx as a target gas to be measured.

The protection cover 130 includes a bottomed cylindrical inner protection cover 131 to cover the front end of the sensor element 101 and a bottomed cylindrical outer protection cover 132 to cover the inner protection cover 131. The inner protection cover 131 and the outer protection cover 132 have a plurality of holes 134 formed to flow a measurement-object gas into the protection cover 130. A sensor element chamber 133 is formed as a space surrounded by the inner protection cover 131, and the front end of the sensor element 101 is disposed in this sensor element chamber 133.

The sensor assembly 140 includes an element sealing body 141 to seal and fix the sensor element 101, a nut 147 attached to the element sealing body 141, an outer cylinder 148, and a connector 150 that is in contact with and electrically connected with connector electrodes (which are not shown, but only a heat connector electrode 71 described later is shown in FIG. 2) formed on the surface (upper and lower surfaces) of the rear end of the sensor element 101.

The element sealing body 141 includes a cylindrical main fitting 142, a cylindrical inner cylinder 143 coaxially fixed to the main fitting 142 by welding, ceramic supporters 144a to 144c encapsulated in a through-hole inside the main fitting 142 and the inner cylinder 143, green compacts 145a and 145b, and a metal ring 146. The sensor element 101 is located on the central axis of the element sealing body 141 and extends through the element sealing body 141 in the front and rear direction. The inner cylinder 143 has a reduced diameter portion 143a for pressing the green compact 145b toward the central axis of the inner cylinder 143 and a reduced diameter portion 143b for pressing forward the ceramic supporters 144a to 144c and the green compacts 145a and 145b via the metal ring 146. The green compacts 145a and 145b are compressed between both the main fitting 142 and the inner cylinder 143 and the sensor element 101 by pressing force from the reduced diameter portions 143a and 143b, and therefore the green compacts 145a and 145b seal the sensor element chamber 133 in the protection cover 130 and a space 149 in the outer cylinder 148 from each other and fix the sensor element 101.

The nut 147 is concentrically fixed to the main fitting 142 and has an external thread formed on an outer peripheral surface thereof. The external thread of the nut 147 is inserted in a fixing member 191 welded to the pipe 190 and having an internal thread in an inner peripheral surface thereof. Thus, the gas sensor 100 is fixed to the pipe 190 in a state where part of the gas sensor 100 such as the front end of the sensor element 101 and the protection cover 130 protrudes into the pipe 190.

The external cylinder 148 surrounds the inner cylinder 143, the sensor element 101, and the connector 150, and a plurality of lead wires 155 connected to the connector 150 are drawn outside from the rear end. These lead wires 155 are electrically connected with electrodes (described later) of the sensor element 101 respectively via the connector 150. A gap between the outer cylinder 148 and the lead wires 155 is sealed with a rubber plug 157. The space 149 in the outer cylinder 148 is filled with air. The rear end of the sensor element 101 is disposed in this space 149.

(Sensor Element)

As shown in FIG. 2, the sensor element 101 is an element in an elongated plate shape, including a base part 102 having such a structure that a plurality of oxygen-ion-conductive solid electrolyte layers are layered. The elongated plate shape also called a long plate shape or a belt shape. The base part 102 has such a structure that six layers, namely, a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO_2$) The solid electrolyte forming these six layers is dense and gastight. These six layers all may have the same thickness, or the thickness may vary among the layers. The layers are adhered to each other with an adhesive layer of a solid electrolyte interposed therebetween, and the base part 102 includes the adhesive layer. While a layer configuration composed of the six layers is illustrated in FIG. 2, the layer configuration in the present invention is not limited to this, and any number of layers and any layer configuration are possible.

The sensor element 101 is manufactured, for example, by stacking ceramic green sheets corresponding to the individual layers after conducting predetermined processing, printing of circuit pattern and the like, and then firing the stacked ceramic green sheets so that they are combined together.

A gas inlet 10 is formed between the lower surface of the second solid electrolyte layer 6 and the upper surface of the first solid electrolyte layer 4 in one end part in the longitudinal direction (hereinafter, referred to as a front end part) of the sensor element 101. A measurement-object gas flow cavity 15, that is, a measurement-object gas flow part is formed in such a form that a first diffusion-rate limiting part 11, a buffer space 12, a second diffusion-rate limiting part 13, a first internal cavity 20, a third diffusion-rate limiting part 30, a second internal cavity 40, a fourth diffusion-rate limiting part 60, and a third internal cavity 61 communicate in this order in the longitudinal direction from the gas inlet 10.

The gas inlet 10, the buffer space 12, the first internal cavity 20, the second internal cavity 40, and the third internal cavity 61 constitute internal spaces of the sensor element 101. Each of the internal spaces is provided in such a manner that a portion of the spacer layer 5 is hollowed out, and the top of each of the internal spaces is defined by the lower surface of the second solid electrolyte layer 6, the bottom of each of the internal spaces is defined by the upper surface of the first solid electrolyte layer 4, and the lateral surface of each of the internal spaces is defined by the lateral surface of the spacer layer 5.

Each of the first diffusion-rate limiting part 11, the second diffusion-rate limiting part 13, and the third diffusion-rate limiting part 30 is provided as two laterally elongated slits (having the longitudinal direction of the openings in the direction perpendicular to the figure in FIG. 2). Each of the first diffusion-rate limiting part 11, the second diffusion-rate limiting part 13, and the third diffusion-rate limiting part 30 may be in such a form that a desired diffusion resistance is created, but the form is not limited to the slits.

The fourth diffusion-rate limiting part 60 is provided as a single laterally elongated slit (having the longitudinal direction of the opening in the direction perpendicular to the figure in FIG. 2) between the spacer layer 5 and the second solid electrolyte layer 6. The fourth diffusion-rate limiting part 60 may be in such a form that a desired diffusion resistance is created, but the form is not limited to the slit.

Between the lower surface of the spacer layer 5 and the upper surface of the third substrate layer 3, a reference gas chamber 43 is provided. The reference gas chamber 43 is a space inside the sensor element 101 and is provided by hollowing out the first solid electrolyte layer 4. In the present embodiment, the reference gas chamber 43 is a space closed inside the base part 102. The reference gas chamber 43 is a region for storing a reference gas used as a reference when the concentration of NOx is measured. The reference gas is a gas having a predetermined oxygen concentration. In the present embodiment, the reference gas is air or a gas having the same oxygen concentration as air (e.g., a gas containing nitrogen as a base gas and oxygen). In the reference gas chamber 43, a reference electrode 42 is disposed.

The reference electrode 42 is an electrode disposed on the upper surface of the third substrate layer 3 in the reference gas chamber 43. As will be described later, the reference electrode 42 can be used to measure the oxygen concentration (oxygen partial pressure) in the first internal cavity 20, the second internal cavity 40, and the third internal cavity 61. The reference electrode 42 is formed as a porous cermet electrode (e.g., a cermet electrode of Pt and $ZrO_2$)

In the measurement-object gas flow cavity 15, the gas inlet 10 is open to the external space, and the measurement-object gas is taken into the sensor element 101 from the external space through the gas inlet 10.

In the present embodiment, the measurement-object gas flow cavity 15 is in such a form that the measurement-object gas is introduced through the gas inlet 10 that is open on the front end surface of the sensor element 101, however, the present invention is not limited to this form. For example, the measurement-object gas flow cavity 15 need not have a recess of the gas inlet 10. In this case, the first diffusion-rate limiting part 11 substantially serves as a gas inlet.

For example, the measurement-object gas flow cavity 15 may have an opening that communicates with the buffer space 12 or a position in the vicinity of the buffer space 12 of the first internal cavity 20, on a lateral surface along the longitudinal direction of the base part 102. In this case, the measurement-object gas is introduced from the lateral surface along the longitudinal direction of the base part 102 through the opening.

Further, for example, the measurement-object gas flow cavity 15 may be so configured that the measurement-object gas is introduced through a porous body.

The first diffusion-rate limiting part 11 creates a predetermined diffusion resistance to the measurement-object gas taken through the gas inlet 10.

The buffer space 12 is provided to guide the measurement-object gas introduced from the first diffusion-rate limiting part 11 to the second diffusion-rate limiting part 13.

The second diffusion-rate limiting part 13 creates a predetermined diffusion resistance to the measurement-object gas introduced into the first internal cavity 20 from the buffer space 12.

It suffices that the amount of the measurement-object gas to be introduced into the first internal cavity 20 finally falls within a predetermined range. That is, it suffices that a predetermined diffusion resistance is created in a whole from the front end part of the sensor element 101 to the second diffusion-rate limiting part 13. For example, the first diffusion-rate limiting part 11 may directly communicate with the first internal cavity 20, or the buffer space 12 and the second diffusion-rate limiting part 13 may be absent.

The buffer space 12 is provided to mitigate the influence of pressure fluctuation on the detected value when the pressure of the measurement-object gas fluctuates.

When the measurement-object gas is introduced from outside the sensor element 101 into the first internal cavity 20, the measurement-object gas, which is rapidly taken through the gas inlet 10 into the sensor element 101 due to pressure fluctuation of the measurement-object gas in the external space (pulsations in exhaust pressure if the measurement-object gas is automotive exhaust gas), is not directly introduced into the first internal cavity 20. Rather, the measurement-object gas is introduced into the first internal cavity 20 after the pressure fluctuation of the measurement-object gas is eliminated through the first diffusion-rate limiting part 11, the buffer space 12, and the second diffusion-rate limiting part 13. Thus, the pressure fluctuation of the measurement-object gas introduced into the first internal cavity 20 becomes almost negligible.

The first internal cavity 20 is provided as a space for adjusting the oxygen partial pressure in the measurement-object gas introduced through the second diffusion-rate limiting part 13. The oxygen partial pressure is adjusted by operation of a main pump cell 21.

The main pump cell 21 is an electrochemical pump cell composed of an inner main pump electrode 22 having a ceiling electrode portion 22a disposed over substantially the entire surface of the lower surface of the second solid electrolyte layer 6 that faces the first internal cavity 20, an outer pump electrode 23 disposed on a region of the upper surface of the second solid electrolyte layer 6 that corresponds to the ceiling electrode portion 22a so as to be exposed to the external space (the sensor element chamber 133 in FIG. 1), and the second solid electrolyte layer 6 sandwiched between the inner main pump electrode 22 and the outer pump electrode 23.

The inner main pump electrode 22 is disposed on an inner surface of the measurement-object gas flow cavity 15 that faces the first internal cavity 20. That is, the inner main pump electrode 22 is formed to span the upper and lower solid electrolyte layers (the second solid electrolyte layer 6 and the first solid electrolyte layer 4) that define the first internal cavity 20 and the spacer layer 5 that defines the lateral wall. Specifically, the ceiling electrode portion 22a is formed on the lower surface of the second solid electrolyte layer 6 that defines the ceiling surface of the first internal cavity 20, and a bottom electrode portion 22b is formed on the upper surface of the first solid electrolyte layer 4 that defines the bottom surface of the first internal cavity 20. Also, lateral electrode portions (not shown) are formed on the lateral wall surfaces (inner surface) of the spacer layer 5 that form both lateral wall parts of the first internal cavity 20 so as to connect the ceiling electrode portion 22a and the bottom electrode portion 22b. Thus, the inner main pump electrode 22 is provided as a tunnel-like structure in the area where the lateral electrode portions are disposed.

The inner main pump electrode 22 and the outer pump electrode 23 are each formed as a porous cermet electrode (e.g., a cermet electrode of Pt containing 1% Au and $ZrO_2$). It is to be noted that the inner main pump electrode 22 to be in contact with the measurement-object gas is formed using a material having a weakened ability to reduce a NOx component in the measurement-object gas.

In the main pump cell 21, a desired pump voltage Vp0 is applied between the inner main pump electrode 22 and the outer pump electrode 23 by a variable power supply 24 to flow a pump current Ip0 between the inner main pump electrode 22 and the outer pump electrode 23 in either a positive or negative direction, and thus it is possible to pump out oxygen in the first internal cavity 20 to the external space or pump oxygen into the first internal cavity 20 from the external space.

To detect the oxygen concentration (oxygen partial pressure) in the atmosphere in the first internal cavity 20, the inner main pump electrode 22, the second solid electrolyte layer 6, the spacer layer 5, the first solid electrolyte layer 4, the third substrate layer 3, and the reference electrode 42 form an electrochemical sensor cell, namely, an oxygen-partial-pressure detection sensor cell 80 for main pump control.

The oxygen concentration (oxygen partial pressure) in the first internal cavity 20 can be detected from an electromotive force (a voltage V0) measured in the oxygen-partial-pressure detection sensor cell 80 for main pump control. In addition, the pump current Ip0 is controlled by performing feedback control of the pump voltage Vp0 so that the voltage V0 is constant. Thus, the oxygen concentration in the first internal cavity 20 can be maintained at a predetermined constant value.

The third diffusion-rate limiting part 30 creates a predetermined diffusion resistance to the measurement-object gas whose oxygen concentration (oxygen partial pressure) has been controlled in the first internal cavity 20 by the operation of the main pump cell 21, and guides the measurement-object gas into the second internal cavity 40.

The second internal cavity 40 is provided as a space for adjusting the oxygen partial pressure in the measurement-object gas introduced through the third diffusion-rate limiting part more accurately. The oxygen partial pressure is adjusted by operation of an auxiliary pump cell 50.

After the oxygen concentration (oxygen partial pressure) in the measurement-object gas is adjusted in advance in the first internal cavity 20, the measurement-object gas is introduced through the third diffusion-rate limiting part 30, and is further subjected to adjustment of the oxygen partial pressure by the auxiliary pump cell 50 in the second internal cavity 40. Thus, the oxygen concentration in the second internal cavity 40 can be kept constant with high accuracy, and the NOx concentration can be measured with high accuracy in the gas sensor 100.

The auxiliary pump cell 50 is an auxiliary electrochemical pump cell composed of an auxiliary pump electrode 51 having a ceiling electrode portion 51a disposed on substantially the entire surface of lower surface of the second solid electrolyte layer 6 facing with the second internal cavity 40, the outer pump electrode 23 (the outer electrode is not limited to the outer pump electrode 23, but may be any suitable electrode outside the sensor element 101), and the second solid electrolyte layer 6.

The auxiliary pump electrode 51 is disposed at a position farther from the one end part (the front end portion) in the longitudinal direction of the base part 102 (the sensor element 101) than the inner main pump electrode 22 on the inner surface of the measurement-object gas flow cavity 15.

This auxiliary pump electrode 51 is disposed in the second internal cavity 40 in a tunnel-like structure similar to the inner main pump electrode 22 disposed in the first internal cavity 20 described previously. Specifically, in the tunnel-like structure, the ceiling electrode portion 51a is formed on the second solid electrolyte layer 6 that defines the ceiling surface of the second internal cavity 40, a bottom electrode portion 51b is formed on the first solid electrolyte layer 4 that defines the bottom surface of the second internal cavity 40, and lateral electrode portions (not shown) connecting the ceiling electrode portion 51a and the bottom electrode portion 51b are formed on the wall surfaces of the spacer layer 5 that define the lateral walls of the second internal cavity 40.

It is to be noted that the auxiliary pump electrode 51 is formed using a material having a weakened ability to reduce a NOx component in the measurement-object gas, as with the case of the inner main pump electrode 22.

In the auxiliary pump cell 50, by applying a desired pump voltage Vp1 between the auxiliary pump electrode 51 and the outer pump electrode 23 by a variable power supply 52, it is possible to pump out oxygen in the atmosphere in the second internal cavity 40 to the external space, or pump the oxygen into the second internal cavity 40 from the external space.

To control the oxygen partial pressure in the atmosphere in the second internal cavity 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an oxygen-partial-pressure detection sensor cell 81 for auxiliary pump control.

The auxiliary pump cell 50 performs pumping with the variable power supply 52 whose voltage is controlled on the basis of an electromotive force (a voltage V1) detected by the oxygen-partial-pressure detection sensor cell 81 for auxiliary pump control. Thus, the oxygen partial pressure in the atmosphere in the second internal cavity 40 is controlled to such a low partial pressure that does not substantially affect measurement of NOx.

In addition, a pump current Ip1 is used for control of the voltage V0 of the oxygen-partial-pressure detection sensor cell 80 for main pump control. Specifically, the pump current Ip1 is input to the oxygen-partial-pressure detection sensor cell 80 for main pump control as a control signal to control the voltage V0, and thus the gradient of the oxygen partial pressure in the measurement-object gas introduced into the second internal cavity 40 from the third diffusion-rate limiting part 30 is controlled to remain constant. In using as a NOx sensor, the oxygen concentration in the second internal cavity 40 is kept at a constant value of about 0.001 ppm by the actions of the main pump cell 21 and the auxiliary pump cell 50.

The fourth diffusion-rate limiting part 60 creates a predetermined diffusion resistance to the measurement-object gas whose oxygen concentration (oxygen partial pressure) has been controlled to further low in the second internal cavity 40 by the operation of the auxiliary pump cell 50, and guides the measurement-object gas into the third internal cavity 61.

The third internal cavity 61 is provided as a space for measuring nitrogen oxide (NOx) concentration in the measurement-object gas introduced through the fourth diffusion-rate limiting part 60. By the operation of a measurement pump cell 41, NOx concentration is measured.

The measurement pump cell 41 measures NOx concentration in the measurement-object gas in the third internal cavity 61. The measurement pump cell 41 includes an inner measurement electrode (in this embodiment, a measurement electrode 44) disposed in the measurement-object gas flow cavity 15 (on the inner surface of the measurement-object gas flow cavity 15) and an outer measurement electrode (in this embodiment, the outer pump electrode 23) disposed at a position different from the measurement-object gas flow cavity 15 on the base part and corresponding to the inner measurement electrode.

That is, in this embodiment, the measurement pump cell 41 is an electrochemical pump cell composed of the measurement electrode 44 disposed on the upper surface of the first solid electrolyte layer 4 facing with the third internal cavity 61, the outer pump electrode 23 (the outer electrode is not limited to the outer pump electrode 23, but may be any suitable electrode outside the sensor element 101), the second solid electrolyte layer 6, the spacer layer 5, and the first solid electrolyte layer 4.

The measurement electrode 44 is disposed at a position farther from the one end part (the front end portion) in the longitudinal direction of the base part 102 (the sensor element 101) than the inner main pump electrode 22 and the auxiliary pump electrode 51 on the inner surface of the measurement-object gas flow cavity 15.

The measurement electrode 44 is a porous cermet electrode. The measurement electrode 44 functions also as a NOx reduction catalyst that reduces NOx present in the atmosphere in the third internal cavity 61. For example, in this embodiment, the measurement electrode 44 is formed as a porous cermet electrode made of Pt and Rh, and $ZrO_2$.

In the measurement pump cell 41, oxygen generated by decomposition of nitrogen oxide in the atmosphere around the measurement electrode 44 is pumped out, and the amount of generated oxygen can be detected as a pump current Ip2.

To detect the oxygen partial pressure around the measurement electrode 44, the first solid electrolyte layer 4, the third substrate layer 3, the measurement electrode 44, and the reference electrode 42 constitute an electrochemical sensor cell, namely an oxygen-partial-pressure detection sensor cell 82 for measurement pump control. A variable power supply 46 is controlled on the basis of an electromotive force (a voltage V2) detected by the oxygen-partial-pressure detection sensor cell 82 for measurement pump control.

The measurement-object gas introduced into the second internal cavity 40 reaches the measurement electrode 44 in the third internal cavity 61 through the fourth diffusion-rate limiting part 60 under the condition that the oxygen partial pressure is controlled. Nitrogen oxide in the measurement-object gas around the measurement electrode 44 is reduced ($2NO \rightarrow N_2 + O_2$) to generate oxygen. The generated oxygen is to be pumped by the measurement pump cell 41, and at this time, a pump voltage Vp2 of the variable power supply 46 is controlled so that the voltage V2 detected by the oxygen-partial-pressure detection sensor cell 82 for measurement pump control is constant. Since the amount of oxygen generated around the measurement electrode 44 is proportional to the concentration of nitrogen oxide in the measurement-object gas, nitrogen oxide concentration in the measurement-object gas is calculated by using the pump current Ip2 in the measurement pump cell 41.

By configuring oxygen partial pressure detecting means by an electrochemical sensor cell composed of a combination of the measurement electrode 44, the first solid electrolyte layer 4, the third substrate layer 3 and the reference electrode 42, it is possible to detect an electromotive force in accordance with a difference between the amount of oxygen generated by reduction of NOx components in the atmosphere around the measurement electrode 44 and the amount of oxygen contained in the reference air, and hence it is possible to determine the concentration of NOx components in the measurement-object gas.

Also, the second solid electrolyte layer 6, the spacer layer 5, the first solid electrolyte layer 4, the third substrate layer 3, the outer pump electrode 23, and the reference electrode 42 constitute an electrochemical sensor cell 83, and it is possible to detect the oxygen partial pressure in the measurement-object gas outside the sensor by an electromotive force (a voltage Vref) obtained by the sensor cell 83.

Further, the second solid electrolyte layer 6, the spacer layer 5, the first solid electrolyte layer 4, the third substrate layer 3, the outer pump electrode 23, and the reference electrode 42 constitute an electrochemical reference gas adjustment pump cell 84. The reference gas adjustment pump cell 84 pumps oxygen by a pump current Ip3 flowing due to a pump voltage Vp3 applied by a power supply circuit 85 that is connected between the outer pump electrode 23 and the reference electrode 42. Thus, the reference gas adjustment pump cell 84 can pump oxygen into a space around the reference electrode 42, that is, the reference gas chamber 43 from a space around the outer pump electrode 23 (the sensor element chamber 133 in FIG. 1), or pump out oxygen from the reference gas chamber 43 to the space around the outer pump electrode 23.

In the gas sensor 100 having such a configuration, the main pump cell 21 and the auxiliary pump cell 50 are operated to supply a measurement-object gas whose oxygen partial pressure is usually kept at a low constant value (the value that does not substantially affect measurement of NOx) to the measurement pump cell 41. Therefore, NOx concentration in the measurement-object gas can be detected on the basis of the pump current Ip2 that flows as a result of pumping out of the oxygen generated by reduction of NOx by the measurement pump cell 41 and is almost in proportion to the concentration of NOx in the measurement-object gas.

The sensor element 101 further includes a heater part 70 that functions as a temperature regulator of heating and maintaining the temperature of the sensor element 101 so as to enhance the oxygen ion conductivity of the solid electrolyte. The heater part 70 includes a heater connector electrode 71, a heater 72, a heater lead 76, a through hole 73, and a heater insulating layer 74.

The heater connector electrode 71 is an electrode formed in contact with the lower surface of the first substrate layer 1. The power can be supplied to the heater part 70 from the outside by connecting the heater connector electrode 71 with a heater power supply that is an external power supply.

The heater 72 is an electrical resistor sandwiched by the second substrate layer 2 and the third substrate layer 3 from top and bottom. The heater 72 is connected with the heater connector electrode 71 via a heater lead 76 that connects with the heater 72 and extends in the rear end side in the longitudinal direction of the sensor element 101, and the through hole 73. The heater 72 is externally powered through the heater connector electrode 71 to generate heat, and heats and maintains the temperature of the solid electrolyte forming the sensor element 101.

The heater 72 is embedded over the whole area from the first internal cavity 20 to the third internal cavity 61 so that the temperature of the sensor element 101 can be adjusted to such a temperature that activates the solid electrolyte. The temperature may be adjusted so that the main pump cell 21, the auxiliary pump cell 50, and the measurement pump cell 41 are operable. It is not necessary that the whole area is adjusted to the same temperature, but the sensor element 101 may have temperature distribution.

In the sensor element 101 of the present embodiment, the heater 72 is embedded in the base part 102, but this form is not limitative. The heater 72 may be disposed to heat the base part 102. That is, the heater 72 may heat the sensor element 101 to develop oxygen ion conductivity with which the main pump cell 21, the auxiliary pump cell 50, and the measurement pump cell 41 are operable. For example, the heater 72 may be embedded in the base part 102 as in the present embodiment. Alternatively, for example, the heater part 70 may be formed as a heater substrate that is separate from the base part 102, and may be disposed at a position adjacent to the base part 102. Alternatively, the sensor element 101 may be heated by a measurement-object gas at high temperature. For accurate measurement, it is preferred that the temperature of the sensor element 101 be constant regardless of the temperature of the measurement-object gas. In consideration of this point, it is preferred that the sensor element 101 include the heater part 70 as in the present embodiment.

The heater insulating layer 74 is formed of an insulator such as alumina on the upper and lower surfaces of the heater 72 and the heater lead 76. The heater insulating layer 74 is formed to ensure electrical insulation between the second substrate layer 2, and the heater 72 and the heater lead 76, and electrical insulation between the third substrate layer 3, and the heater 72 and the heater lead 76.

(Control Unit)

The gas sensor 100 of this embodiment includes the sensor element 101 described above and the control unit 90 for controlling the sensor element 101. In the gas sensor 100, each of the electrodes 22, 23, 51, 44, and 42 of the sensor element 101 is electrically connected to the control unit 90 through the lead wire 155. FIG. 3 is a block diagram showing electric connections between the control unit 90, and the respective pump cells 21, 50, 41 and 84, and the respective sensor cells 80, 81, 82, and 83 of the sensor element 101. The control unit 90 includes the above-described variable power supplies 24, 46, and 52 and a power supply circuit 85 and a control part 91. The control part 91 includes a drive control part 92, a storing part 93, and a diagnosing part 94.

The control part 91 is realized by a general-purpose or dedicated computer, and functions as the drive control part 92, the storing part 93, and the diagnosing part 94 are realized by a CPU, a memory or the like installed in the computer. It is to be noted that when NOx contained in exhaust gas from the engine of a car is a target gas to be measured by the gas sensor 100 and the sensor element 101 is attached to an exhaust gas path, some or all of the functions of the control unit 90 (especially, the control part 91) may be realized by an electronic control unit (ECU) installed in the car.

The control part 91 is configured to acquire an electromotive force (a voltage V0, V1, V2, or Vref) in each of the sensor cells 80, 81, 82, and 83, and a pump current (Ip0, Ip1, Ip2, or Ip3) in each of the pump cells 21, 50, 41 and 84 of the sensor element 101. Further, the control part 91 is configured to output control signals to the variable power supplies 24, 52 and 46, and the power supply circuit 85, and a control part 91. The control part 91 includes a driving control part 92, a storing part 93, and a determining part 95.

The drive control part 92 is configured to control the operation of the main pump cell 21, the auxiliary pump cell 50 and the measurement pump cell 41. Further, the drive control part 92 may be configured to control the operation of the reference gas adjustment pump cell 84.

The driving control part 92 performs a normal control for detecting a target gas to be measured in a measurement-object gas by operating a pump cell including an intra-cavity electrode disposed in the measurement-object gas flow cavity 15 and an extra-cavity electrode disposed at a position different from the measurement-object gas flow cavity 15 on the base part and corresponding to the intra-cavity electrode.

The intracavity electrode is an electrode disposed in the measurement-object gas flow cavity 15, that is, on the inner surface of the measurement-object gas flow cavity 15. The measurement-object gas whose amount is adjusted by the diffusion-rate limiting part reaches the intracavity electrode. In the present embodiment, the inner main pump electrode 22, the auxiliary pump electrode 51, or the measurement electrode 44 functions as the intracavity electrode. In the present embodiment, the main pump cell 21, the auxiliary pump cell 50, or the measurement pump cell 41 functions as the pump cell. In the present embodiment, the outer pump electrode 23 functions also as the extracavity electrode of each of the pump cells 21, 50, and 41. In the present embodiment, the driving control part 92 operates the main pump cell 21, the auxiliary pump cell 50, and the measurement pump cell 41 in the normal control.

In the normal control, the driving control part 92 applies a pump current Ip2 between the measurement electrode 44 as an inner measurement electrode and the outer pump electrode 23 that functions as an outer measurement electrode so that the voltage V2 between the measurement electrode 44 and the reference electrode 42 is a target voltage (set value) to measure the concentration of a target gas to be measured (in the present embodiment, NOx) in a measurement-object gas based on a value of the pump current Ip2. More specifically, in the present embodiment, the normal control is performed in the following manner.

The drive control part 92 performs feedback control of the pump voltage Vp0 of the variable power supply 24 in the main pump cell 21 so that the voltage V0 in the oxygen-partial-pressure detection sensor cell 80 for main pump control is at a constant value (referred to as a set value $V0_{SET}$). The voltage V0 indicates the oxygen partial pressure in the vicinity of the inner main pump electrode 22, and therefore making the voltage V0 constant means that the oxygen partial pressure in the vicinity of the inner main pump electrode 22 is made constant. As a result, the pump current Ip0 in the main pump cell 21 varies depending on the oxygen concentration in the measurement-object gas.

When the oxygen partial pressure in the measurement-object gas is higher than the oxygen partial pressure corresponding to the set value $V0_{SET}$, the main pump cell 21 pumps oxygen out from the first internal cavity 20. On the other hand, when the oxygen partial pressure in the measurement-object gas is lower than the oxygen partial pressure corresponding to the set value $V0_{SET}$ (for example, when hydrocarbons HC or the like are contained), the main pump cell 21 pumps oxygen into the first internal cavity 20 from the space outside the sensor element 101. Therefore, the value of the pump current Ip0 may be either positive or negative.

The drive control part 92 performs feedback control of the pump voltage Vp1 of the variable power supply 52 in the auxiliary pump cell 50 so that the voltage V1 in the oxygen-partial-pressure detection sensor cell 81 for auxiliary pump control is at a constant value (referred to as a set value $V1_{SET}$). The voltage V1 indicates the oxygen partial pressure in the vicinity of the auxiliary pump electrode 51, and therefore making the voltage V1 constant means that the oxygen partial pressure in the vicinity of the auxiliary pump electrode 51 is made constant. The oxygen partial pressure in the atmosphere in the second internal space 40 is thereby controlled to be a low partial pressure that does not substantially affect measurement of NOx.

At the same time, feedback control is performed to set the set value $V0_{SET}$ of the voltage V0 on the basis of the pump current Ip1 in the auxiliary pump cell 50 so that the pump current Ip1 is at a constant value (referred to as a set value $Ip1_{SET}$). Specifically, the pump current Ip1 is input, as a control signal, to the oxygen-partial-pressure detection sensor cell 80 for main pump control, and the voltage V0 therein is controlled to be the set value $V0_{SET}$ set on the basis of the pump current Ip1 so that the oxygen partial pressure in the measurement-object gas introduced through the third diffusion-rate limiting part 30 into the second internal cavity 40 is controlled to have a gradient that is always constant. In use as the NOx sensor, the oxygen concentration in the second internal cavity 40 is maintained at a constant value of approximately 0.001 ppm by the action of the main pump cell 21 and the auxiliary pump cell 50. That is to say, the oxygen concentration in the measurement-object gas introduced through the fourth diffusion-rate limiting part 60 into the third internal cavity 61 is considered to be maintained at a constant value of approximately 0.001 ppm.

The drive control part 92 performs feedback control of the pump voltage Vp2 of the variable power supply 46 in the measurement pump cell 41 so that the voltage V2 detected in the oxygen-partial-pressure detection sensor cell 82 for measurement pump control is at a constant value (referred to as a set value $V2_{SET}$). In the measurement electrode 44, nitrogen oxide in the measurement-object gas is reduced ($2NO{\rightarrow}N_2+O_2$) to generate oxygen. The generated oxygen is pumped out by the measurement pump cell 41 so that the voltage V2 becomes the set value $V2_{SET}$. The set value $V2_{SET}$ can be set as a value such that substantially all of NOx is decomposed at the measurement electrode 44. The set value $V2_{SET}$ can be set as a value such that the pump current Ip2 is at a limiting current. The limiting current will be described later.

The driving control part 92 may further perform a control to apply a pump voltage Vp3 by the power supply circuit 85 to the reference gas adjustment pump cell 84 to flow a pump current Ip3. By flowing a pump current Ip3, pumping of oxygen into the reference gas chamber 43 (oxygen pump-in control) or pumping out of oxygen from the reference gas chamber 43 (oxygen pump-out control) may be performed. In the normal control, for example, a control to apply a predetermined pump voltage Vp3 or a control to apply a predetermined pump current Ip3 may be performed. When such a control is performed in the normal control, for example, the pump current Ip3 may be applied continuously or intermittently. The pump current Ip3 may be constant or may vary. When the oxygen pump-in control or the oxygen pump-out control is performed in the normal control, attention should be paid so that such a control is performed with virtually no influence on measurement accuracy.

As described later, at a diagnostic time at which the diagnosing part 94 diagnoses a reference potential of the reference electrode 42, the driving control part 92 may stop the above-described normal control of each of the pump cells 21, 50, 41, and 84.

The storing part 93 stores in advance, a standard voltage current correspondence relationship (standard correspondence relationship) of a voltage between the intracavity electrode and the reference electrode 42 with a current flowing through the pump cell (between the intracavity electrode and the extracavity electrode) at a time at which the reference potential of the reference electrode 42 is at a predetermined value (referred to as a standard time). In the sensor element 101 according to the present embodiment, the pump cell is the main pump cell 21, the auxiliary pump cell 50, or the measurement pump cell 41. The intracavity electrodes of these pump cells are the inner main pump electrode 22, the auxiliary pump electrode 51, and the measurement electrode 44, respectively. In any of the pump cells, the extracavity electrode is the outer pump electrode 23. For example, in the present embodiment, a standard correspondence relationship of a voltage V2 between the measurement electrode 44 and the reference electrode 42 with a pump current Ip2 flowing through the measurement pump cell 41 (between the measurement electrode 44 and the outer pump electrode 23) is stored in advance. The diagnosing part 94 described later diagnoses a reference potential of the reference electrode 42 using the standard correspondence relationship stored in the storing part 93.

The diagnosing part 94 obtains a diagnostic voltage current correspondence relationship (diagnostic correspondence relationship) of a voltage (voltage V2) between the intracavity electrode (measurement electrode 44) and the reference electrode 42 with a current (pump current Ip2) flowing through the pump cell (in the present embodiment, the measurement pump cell 41) at a diagnostic time at which a reference potential of the reference electrode 42 is diagnosed, and compares the obtained diagnostic correspondence relationship with the standard correspondence relationship stored in advance in the storing part to diagnose a deviation of the reference potential of the reference electrode 42 at the diagnostic time from the predetermined value at the standard time. Based on the diagnosed deviation, the diagnosing part 94 can correct the deviation. The diagnosis and correction performed by the diagnosing part 94 will be described later in detail.

The standard correspondence relationship stored in the storing part 93 and the diagnostic correspondence relationship obtained by the diagnosing part 94 will be described later in detail.

[Production of Gas Sensor]

Hereinbelow, an example of a method for producing such a gas sensor 100 as described above will be described. The sensor element 101 can be produced by performing predetermined processing, circuit pattern printing and the like on each of unfired sheet-shaped molded products (so-called green sheets) containing an oxygen-ion-conductive solid electrolyte such as zirconia ($ZrO_2$) as a ceramic component, laminating these sheets, cutting the laminated body, and firing the resultant. Then, the gas sensor 100 incorporating the sensor element 101 is produced.

Hereinafter, description is made while taking the case of manufacturing the sensor element 101 composed of six layers shown in FIG. 2 as an example.

First, six green sheets containing an oxygen-ion-conductive solid electrolyte such as zirconia ($ZrO_2$) as a ceramic component are prepared. For manufacturing of the green sheets, a known molding method can be used. The six green sheets may all have the same thickness, or the thickness differs depending on the layer to be formed. In each of the six green sheets, sheet holes or the like for use in positioning at the time of printing or stacking are formed in advance by a known method such as a punching process with a punching apparatus (blank sheet). In the blank sheet for use as the spacer layer 5, penetrating parts such as internal cavities are also formed in the same manner. Also in the remaining layers, necessary penetrating parts are formed in advance.

The blank sheets for use as six layers, namely, the first substrate layer 1, the second substrate layer 2, the third substrate layer 3, the first solid electrolyte layer 4, the spacer layer 5, and the second solid electrolyte layer 6 are subjected to printing of various patterns required for respective layers and drying treatment. For printing of a pattern, a known screen printing technique can be used. Also as the drying treatment, a known drying means can be used.

After completing the printing and drying of diverse patterns for each of the six blank sheets by repeating these steps, contact bonding treatment of stacking the six printed blank sheets in a predetermined order while positioning with the sheet holes and the like, and contact bonding at a predetermined temperature and pressure condition to give a laminate is conducted. The contact bonding treatment is conducted by heating and pressurizing with a known laminator such as a hydraulic press. While the temperature, the pressure and the time of heating and pressurizing depend on the laminator being used, they may be appropriately determined to achieve excellent lamination.

The obtained laminate includes a plurality of sensor elements 101. The laminate is cut into units of the sensor element 101. The cut laminate is fired at a predetermined firing temperature to obtain the sensor element 101. The firing temperature may be such a temperature that the solid electrolyte forming the base part 102 of the sensor element 101 is sintered to become a dense product, and electrodes or the like maintains desired porosity. The firing is conducted, for example, at a firing temperature of about 1300 to 1500° C.

Then, the gas sensor 100 incorporating the sensor element 101 is produced. For example, the element sealing body 141 is attached to the sensor element 101 to seal and fix the sensor element 101, and the connector 150 and the lead wires 155 are attached to the rear end side of the sensor element 101 to be electrically connected with the connector electrodes such as the heat connector electrode 71. Further, the protection cover 130 is attached to the element sealing body 141 on the front end side of the sensor element 101. Further, the outer cylinder 148 is attached to the element sealing body 141 on the rear end side of the sensor element 101, and the lead wires 155 are drawn out from the outer cylinder 148. The control unit 90 and the sensor element 101 are connected via the lead wires 155. In this way, the gas sensor 100 is obtained.

The production process of the gas sensor 100 preferably includes, after the sensor element 101 or the gas sensor 100 is obtained, an oxygen concentration confirming step in which the oxygen concentration in the reference gas chamber 43 is confirmed and, if necessary, the oxygen concentration in the reference gas chamber 43 is adjusted. This step is performed in, for example, the following manner. First, the sensor element 101 is maintained at a predetermined driving temperature (e.g., 800° C.) and a voltage Vref of the sensor cell 83 is measured in a state where the outer pump electrode 23 of the sensor element 101 is in contact with a gas having a known oxygen concentration (e.g., air). Then, the oxygen concentration in the reference gas chamber 43 is derived based on the known oxygen concentration and the voltage Vref. Then, the oxygen concentration in the reference gas chamber 43 is confirmed to fall within a predetermined oxygen concentration range regarded as the same as the oxygen concentration in a reference gas. When the oxygen concentration in the reference gas chamber 43 falls outside the predetermined oxygen concentration range, a pump current Ip3 is applied by applying a pump voltage Vp3 from the power supply circuit 85 to the reference gas adjustment pump cell 84 to pump oxygen into the reference gas chamber 43 or pump out oxygen from the reference gas chamber 43. In this way, the oxygen concentration in the reference gas chamber 43 is adjusted to fall within the predetermined oxygen concentration range. The measurement of the voltage Vref and the adjustment of the oxygen concentration in the reference gas chamber 43 may be performed by the control unit 90 of the gas sensor 100 or by another device that is different from the control unit 90 and is connected to the sensor element 101.

At the time of measuring the voltage Vref in the oxygen concentration confirming step, a pump voltage Vp3 is not applied to the reference gas adjustment pump cell 84. Further, at the time of measuring the voltage Vref, it is preferred that a control to apply a current to the outer pump electrode 23 is not performed on the sensor element 101 to reduce a measurement error due to voltage drop of the outer pump electrode 23 and the reference electrode 42. Specifically, it is preferred that the operations of the main pump cell 21, the auxiliary pump cell 50, and the measurement pump cell 41 are stopped (the variable power supplies 24, 52, and 46 do not apply pump voltages Vp0, Vp1, and Vp2). Particularly, the pump current Ip0 flowing through the main pump cell 21 is relatively larger than the pump currents Ip1 and Ip2, and therefore the voltage drop of the outer pump electrode 23 is large. Therefore, among the main pump cell 21, the auxiliary pump cell 50, and the measurement pump cell 41, the operation of at least the main pump cell 21 is preferably stopped.

The production process of the gas sensor 100 preferably further includes, after the oxygen concentration confirming step, a correspondence relationship storing step in which the storing part 93 stores a standard correspondence relationship of a voltage between the intracavity electrode and the reference electrode 42 with a current flowing through the pump cell (between the intracavity electrode and the extracavity electrode) at a standard time at which the reference potential of the reference electrode 42 is at a predetermined value. This step is performed in, for example, the following manner. First, the sensor element 101 is maintained at a predetermined driving temperature (e.g., 800° C.), and the operations of the main pump cell 21, the auxiliary pump cell 50, the measurement pump cell 41, and the reference gas adjustment pump cell 84 in the normal control are stopped. The variable power supply 46 applies a pump voltage Vp2 to the measurement pump cell 41. At this time, a voltage V2 of the oxygen partial pressure detection sensor cell 82 for measurement pump control (between the measurement electrode 44 and the reference electrode 42) and a pump current Ip2 flowing through the measurement pump cell 41 are obtained while the pump voltage Vp2 is swept within a predetermined range to obtain a standard correspondence relationship (e.g., a standard voltage current curve described later) of the voltage V2 with the pump current Ip2. Then, the obtained standard correspondence relationship is stored in the storing part 93.

The standard correspondence relationship may be obtained in each individual gas sensor 100 produced and may be stored in the storing part 93 of the gas sensor 100. Alternatively, a typical standard correspondence relationship may previously be obtained and stored in the storing parts 93 of a plurality of gas sensors 100. For example, the same standard correspondence relationship may be stored in gas sensors 100 having the same configuration or gas sensors 100 of the same production batch. In this case, the correspondence relationship storing step may be performed before the oxygen concentration confirming step.

The standard correspondence relationship may be obtained in the same gas atmosphere (e.g., air) as the oxygen concentration confirming step or a different gas atmosphere from the oxygen concentration confirming step.

The control unit 90 may perform the oxygen concentration confirming step and the subsequent correspondence relationship storing step during the use of the gas sensor 100 in a state where the oxygen concentration in a measurement-object gas is previously known. For example, when the measurement-object gas is exhaust gas from the internal combustion engine of a car or the like, the oxygen concentration in the measurement-object gas can be regarded as the same as air at the time of fuel cutoff of the internal combustion engine, and therefore the same oxygen concentration confirming step as described above may be performed. It is more preferred that the correspondence relationship storing step is performed in the production process, that is, before shipment because diagnosis and correction processing described later can be performed at any timing from the beginning of use of the gas sensor.

[Diagnosis and Correction Processing]

(Voltage Current Curve)

Figure 4:
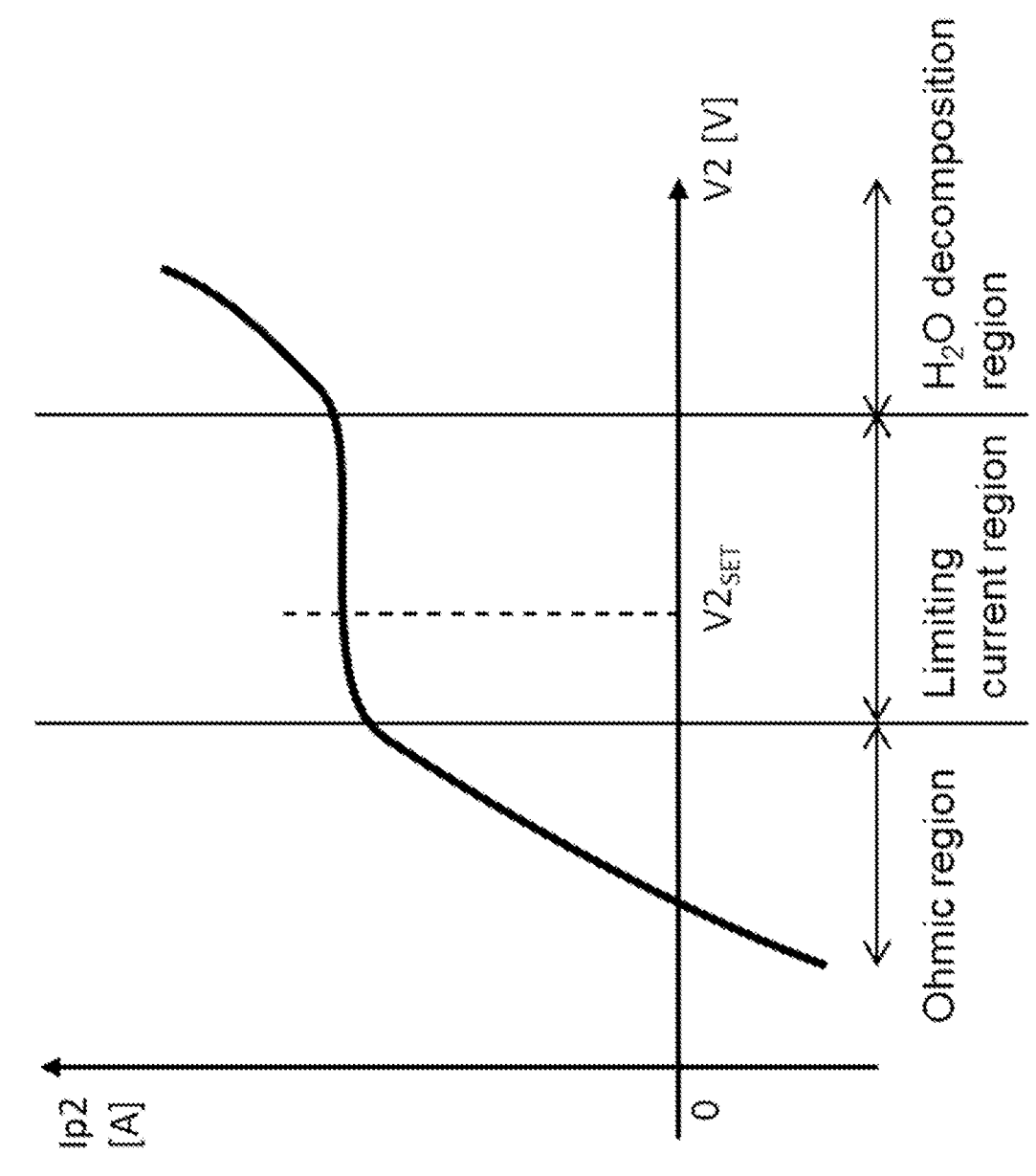
FIG. 4 is a schematic diagram of a voltage current curve showing the correspondence relationship of a voltage V2 between a measurement electrode 44 and a reference electrode 42 with a pump current Ip2 between the measurement electrode 44 and a outer pump electrode 23.

First, voltage current characteristics of the intracavity electrode of the sensor element 101 will be described with reference to a case where the intracavity electrode is the measurement electrode 44. FIG. 4 is a schematic diagram of a voltage current curve showing the correspondence relationship of a voltage V2 between the measurement electrode 44 and the reference electrode 42 with a pump current Ip2 between the measurement electrode 44 and the outer pump electrode 23. In FIG. 4, the horizontal axis represents a voltage V2 [V] and the vertical axis represents a pump current Ip2 [A]. Such a voltage current curve is measured in a state where the sensor element 101 is maintained at a predetermined driving temperature (e.g., 800° C.). The voltage current curve is obtained by obtaining a voltage V2 between the measurement electrode 44 and the reference electrode 42 and a pump current Ip2 flowing between the measurement electrode 44 and the outer pump electrode 23 while sweeping, within a predetermined range, a voltage Vp2 applied by the variable power supply 46 between the measurement electrode 44 and the outer pump electrode 23.

Referring to FIG. 4, a pump voltage Vp2 is first applied between the measurement electrode 44 and the outer pump electrode 23 so that oxygen is pumped into the third internal cavity 61. The applied pump voltage Vp2 is gradually brought close to zero. Then, the pump voltage Vp2 is gradually increased from zero in a direction for pumping out oxygen from the third internal cavity 61. As a result, both of the pump current Ip2 and the voltage V2 between the measurement electrode 44 and the reference electrode 42 gradually increase. A region in which the relationship of the pump current Ip2 with the voltage V2 is linear is referred to as an ohmic region. In the ohmic region, oxygen in an amount proportional to the applied pump voltage Vp2 is pumped into the third internal cavity 61 or pumped out from the third internal cavity 61.

When the pump voltage Vp2 is further gradually increased, the pump current Ip2 reaches its upper limit and therefore does not increase even when the pump voltage Vp2 is increased. The current at this time is referred to as a limiting current. A region in which the pump current Ip2 is a limiting current while the voltage V2 increases is referred to as a limiting current region. In the measurement electrode 44, $O_2$ and NOx exhibit almost the same decomposition behavior. In the limiting current region, the pump current Ip2 proportionate to the amount of oxygen ($O_2$ and/or oxygen derived from NOx) in a measurement-object gas that reaches the third internal cavity 61, that is, the limiting current flows, and the oxygen concentration in the third internal cavity 61 is considered to become substantially zero or sufficiently low.

When the pump voltage Vp2 is further gradually increased, the pump current Ip2 starts to again become larger than the limiting current and linearly increases as the voltage V2 increases. The reason for this is considered to be that water ($H_2O$) in an atmosphere gas around the measurement electrode 44 is decomposed. Such a region is referred to as an $H_2O$ decomposition region.

In the above-described normal control, the set value $V2_{SET}$ may be set to fall within the limiting current region of the voltage current curve. By setting the set value $V2_{SET}$ in such a manner, a limiting current flows as a pump current Ip2 in the normal control. In the normal control, a measurement-object gas having a low oxygen partial pressure that does not substantially affect measurement of NOx reaches the measurement electrode 44. Therefore, a NOx concentration can accurately be detected because a limiting current well corresponds to the NOx concentration in a measurement-object gas.

The voltage V2 between the measurement electrode 44 and the reference electrode 42 generally corresponds to a potential difference generated depending on an oxygen concentration difference between the measurement electrode 44 and the reference electrode 42. Therefore, the concentration of oxygen near the measurement electrode 44 in the third internal cavity 61 can be measured using, as a reference, the oxygen concentration in a reference gas in contact with the reference electrode 42. The voltage V0 between the inner main pump electrode 22 and the reference electrode 42, the voltage V1 between the auxiliary pump electrode 51 and the reference electrode 42, and the voltage Vref between the outer pump electrode 23 and the reference electrode 42 are also measured using, as a reference, the reference electrode 42.

When the oxygen concentration in a reference gas changes for any reason, the electric potential (reference potential) of the reference electrode 42 also changes in response to such a change. As a result, the voltages V0, V1, V2, and Vref in the respective sensor cells 80, 81, 82, and 83 detected using the reference electrode 42 as a reference change. Thus, the detection accuracy of the NOx concentration in a measurement-object gas may reduce.

For example, in the present embodiment, the reference gas chamber 43 is a space substantially closed inside the base part 102. Therefore, flowing of gas into the reference gas chamber 43 from the outside of the sensor element 101 and flowing out of gas from the reference gas chamber 43 are both prevented. However, when, as described above, the voltages V0, V1, V2, and Vref in the respective sensor cells 80, 81, 82, and 83 are measured in the normal control, a minute current flows through each of the sensor cells 80, 81, 82, and 83 because of a voltage measuring circuit such as an electrometer. Therefore, it is considered that oxygen is electrochemically pumped into the reference gas chamber 43 or pumped out from the reference gas chamber 43 due to the minute current. As a result, the oxygen concentration in a reference gas in the reference gas chamber 43 may change. The gas sensor according to the present invention can diagnose such a change in the oxygen concentration in a reference gas and if necessary can perform correction (diagnosis and correction processing). This makes it possible to prevent a reduction in the detection accuracy of the NOx concentration in a measurement-object gas to maintain high measurement accuracy.

(Diagnosis and Correction Processing)

The diagnosis and correction processing performed by the gas sensor according to the present invention will be described below in detail.

In the gas sensor 100, the diagnosing part 94 diagnoses a change in the reference potential of the reference electrode 42 due to a change in the oxygen concentration in a reference gas. Based on the result of the diagnosis, the reference potential can be corrected. This makes it possible to prevent a reduction in the detection accuracy of the NOx concentration in a measurement-object gas.

A deviation of the reference potential is diagnosed by comparing the correspondence relationship of a voltage between the intracavity electrode and the reference electrode 42 with a current flowing through the pump cell (between the intracavity electrode and the extracavity electrode) between a standard time at which the reference potential of the reference electrode 42 is at a predetermined value and a diagnostic time at which the reference potential of the reference electrode 42 is diagnosed. As the correspondence relationship, the voltage current curve described above may be used. Alternatively, part of the voltage current curve may be used. Further, alternatively, a single point of the voltage current curve may be used. The present embodiment will specifically be described below.

In the present embodiment, a deviation of the reference potential is diagnosed using the correspondence relationship of a pump current Ip2 flowing through the measurement pump cell 41 (between the measurement electrode 44 and the outer pump electrode 23) with a voltage V2 between the measurement electrode 44 and the reference electrode 42.

Figure 5:
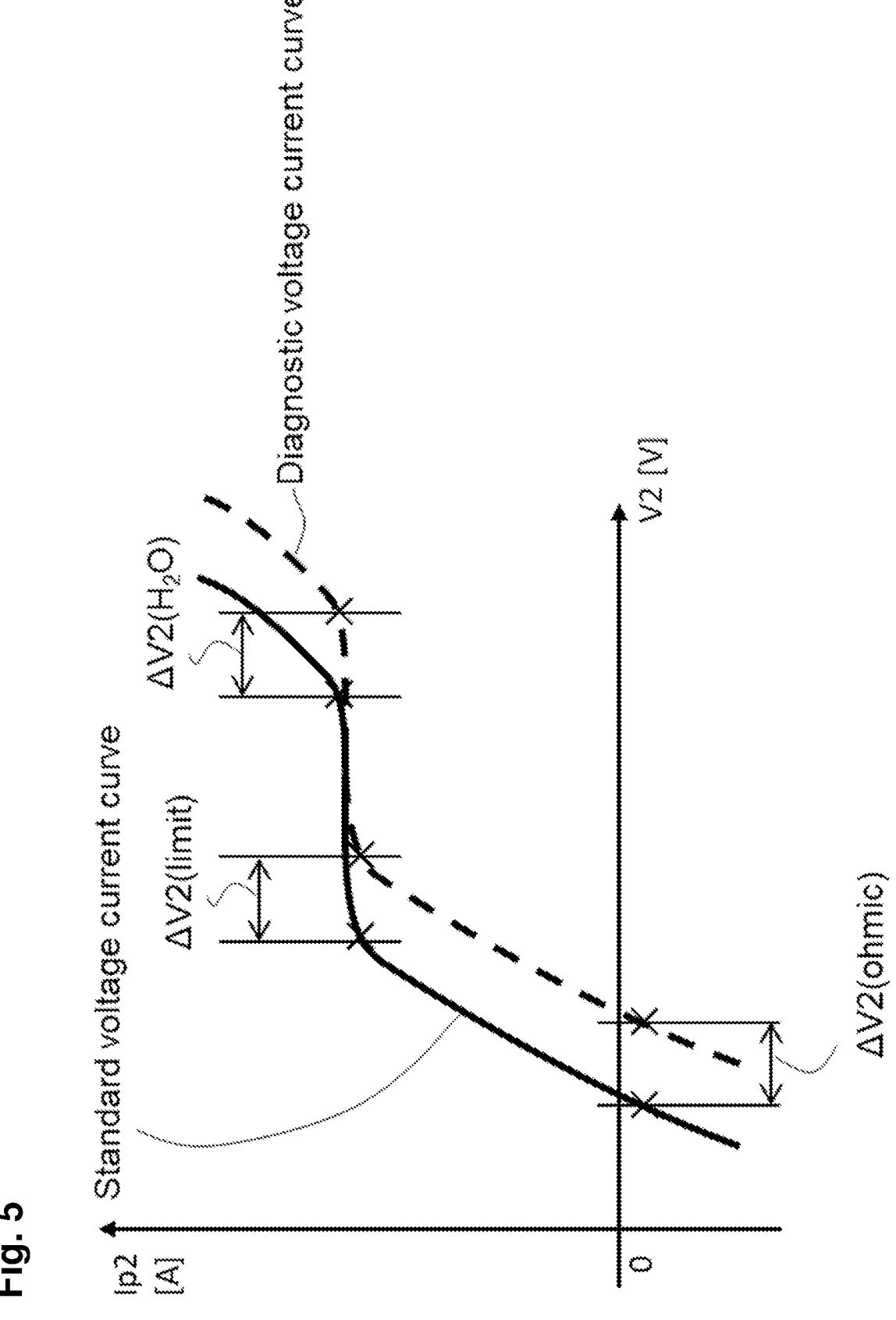
FIG. 5 is a schematic diagram showing an example of a deviation of a diagnostic voltage current curve from a standard voltage current curve.

FIG. 5 is a schematic diagram showing an example of a deviation of a diagnostic voltage current curve from a standard voltage current curve. In FIG. 5, the horizontal axis represents a voltage V2 [V] and the vertical axis represents a pump current Ip2 [A]. When the reference potential of the reference electrode 42 at the diagnostic time deviates from the reference potential at the standard time, as shown in FIG. 5, the voltage current curve shifts in the direction of the horizontal axis. The deviation of the reference potential of the reference electrode 42 is considered to be almost a deviation of the oxygen concentration in a reference gas. For example, when the oxygen concentration in a reference gas is higher than a predetermined concentration (e.g., an oxygen concentration comparable to that of air), the voltage current curve shifts to the right. On the other hand, for example, when the oxygen concentration in a reference gas is lower than a predetermined concentration, the voltage current curve shifts to the left. FIG. 5 shows an example in which the oxygen concentration in a reference gas is higher than a predetermined concentration. It is noted that for explanatory convenience, the diagnostic voltage current curve shown in FIG. 5 is one obtained using a measurement-object gas having the same composition as that used when the standard voltage current curve is obtained, but the diagnostic voltage current curve is not limited thereto. The concentration of oxygen and/or NOx in a measurement-object gas may be different between the standard time and the diagnostic time. In this case, the current value of a limiting current is different between the current voltage curves. That is, in FIG. 5, the diagnostic voltage current curve deviates from the standard voltage current curve in the direction of the vertical axis.

When the voltage current curve shifts as shown in FIG. 5, the set value $V2_{SET}$ in the normal control may deviate from the limiting current region and fall within the ohmic region. In such a case, the pump current Ip2 becomes a current value lower than a limiting current that should flow in response to the NOx concentration so that the detection accuracy of the NOx concentration may reduce. Similarly, the pump current Ip0 flowing through the main pump cell 21 and the pump current Ip1 flowing through the auxiliary pump cell 50 may deviate from the limiting current region. As a result, a measurement-object gas introduced into the third internal cavity 61 may contain oxygen $O_2$ in an amount larger than that at the standard time. In this case, the detection accuracy of the NOx concentration may reduce. As described above, the inner main pump electrode 22 and the auxiliary pump electrode 51 are formed using a material having a weakened ability to reduce a NOx component in a measurement-object gas. However, when the reference potential of the reference electrode 42 deviates from the reference potential at the standard time, the pump voltages Vp0 and Vp1 applied in the main pump cell 21 and the auxiliary pump cell 50 may excessively be large. In such a case, the detection accuracy of the NOx concentration may reduce due to the decomposition of part of NOx in a measurement-object gas in the inner main pump electrode 22 and/or the auxiliary pump electrode 51. However, the reference potential of the reference electrode 42 can be corrected by performing diagnosis and correction processing described below, which makes it possible to prevent a reduction in detection accuracy.

The storing part 93 stores, in advance, a standard voltage current curve. For example, the correspondence relationship storing step described above can be performed in the production process. Alternatively, as described above, a standard voltage current curve may be obtained and stored in the storing part 93 when the reference potential of the reference electrode 42 is confirmed to be at a predetermined value at a timing at which the concentration of oxygen is known, such as the time of fuel cutoff, during the use of the gas sensor 100. Further, the standard voltage current curve may be updated at any timing.

The storing part 93 may store, as a standard correspondence relationship, at least a correspondence relationship similar to the diagnostic correspondence relationship that should be obtained by the diagnosing part 94 at the diagnostic time. For example, the storing part 93 may store a standard voltage current curve in which the electromotive force V2 or the pump current Ip2 is within a predetermined range. The stored standard voltage current curve does not need to contain all the above-described ohmic region, limiting current region, and $H_2O$ decomposition region, and part of the regions of the voltage current curve may be stored. Alternatively, a predetermined single point on the voltage current curve may be stored.

Figure 6:
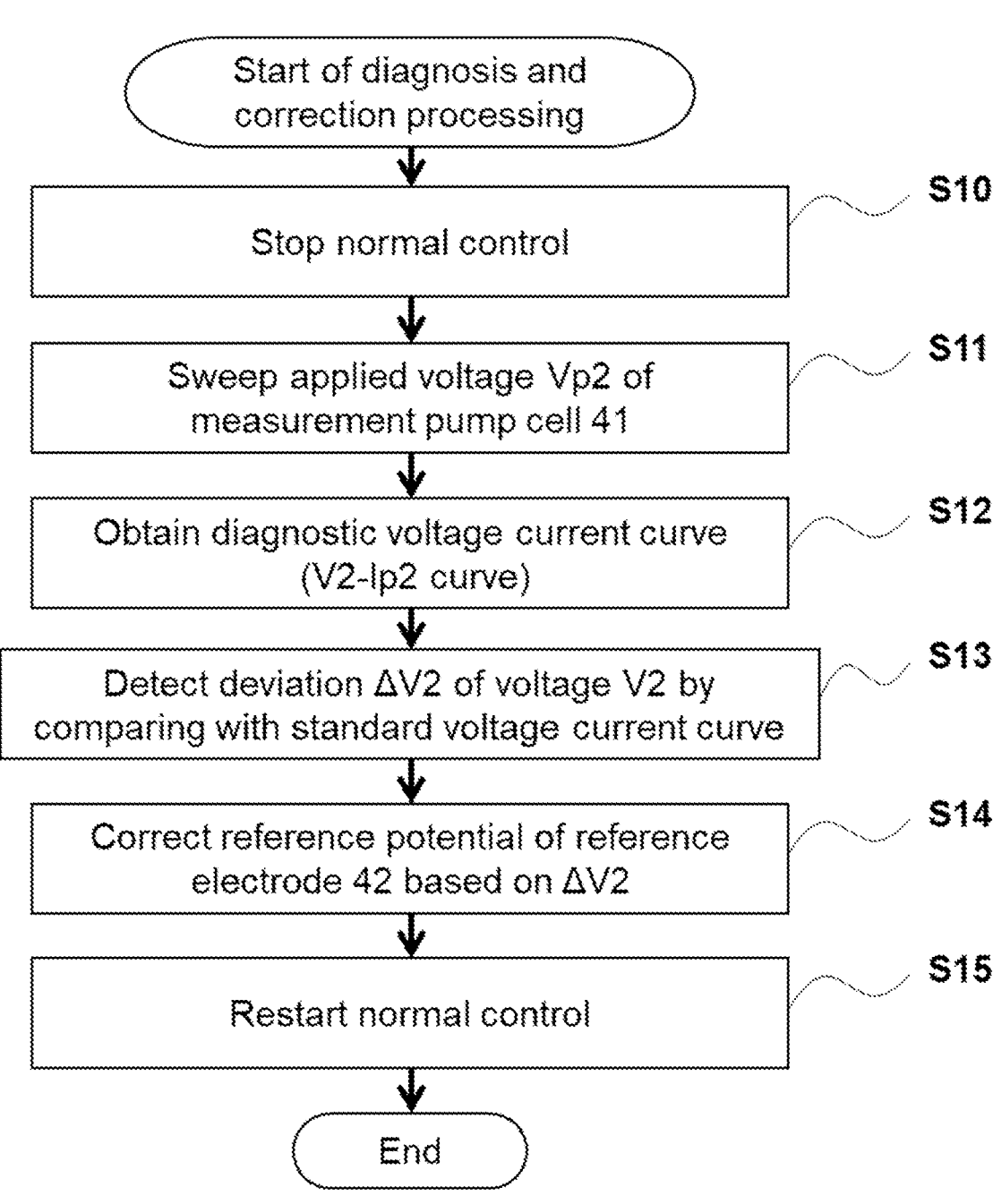
FIG. 6 is a flowchart showing an example of a diagnosis and correction processing.

In a state where the storing part 93 stores a standard correspondence relationship such as a standard voltage current curve, the diagnosing part 94 performs diagnosis and correction processing. FIG. 6 is a flowchart showing an example of the diagnosis and correction processing. The diagnosis and correction processing may be performed at any timing. For example, the diagnosis and correction processing may be performed at a predetermined time interval (e.g., every 50 hours or every 100 hours). Alternatively, for example, the diagnosis and correction processing may be performed when an operator inputs a start command of the diagnosis and correction processing. Alternatively, for example, the diagnosis and correction processing may be performed at the time of a predetermined event such as the activation of the gas sensor 100.

When the diagnosis and correction processing starts, the driving control part 92 stops the normal control (step S10). Specifically, all the pump controls such as a control to feed back a pump voltage Vp0 of the main pump cell 21 so that the voltage V0 is at a set value $V0_{SET}$, a control to feed back a pump voltage Vp1 of the auxiliary pump cell 50 so that the voltage V1 is at a set value $V1_{SET}$, and a control to feed back a pump voltage Vp2 of the measurement pump cell 41 so that the voltage V2 is at a set value $V2_{SET}$ are stopped. That is, controls other than a control to maintain the sensor element 101 at a predetermined temperature by the heater 72 are not performed. Therefore, during the execution of the diagnosis and correction processing, the measurement of the NOx concentration in a measurement-object gas is stopped.

Then, the diagnosing part 94 applies a pump voltage Vp2 to the measurement pump cell 41 and sweeps the pump voltage Vp2 within a predetermined range (step S11). Then, a diagnostic voltage current curve (V2-Ip2 curve) of a pump current Ip2 flowing through the measurement pump cell 41 and a voltage V2 between the measurement electrode 44 and the reference electrode 42 is obtained (step S12).

The diagnosing part 94 reads out a standard voltage current curve from the storing part 93. Then, the diagnosing part 94 compares the diagnostic voltage current curve obtained in step S12 with the standard voltage current curve to calculate a deviation $\Delta V2$ of the voltage V2 (step S13). As described above, when the reference potential of the reference electrode 42 deviates from the reference potential at the standard time, the diagnostic voltage current curve shifts in the direction of the horizontal axis. That is, the deviation $\Delta V2$ of the voltage V2 almost corresponds to a deviation of the reference potential of the reference electrode 42. The reference potential of the reference electrode 42 at the diagnostic time can deviate in either positive or negative direction when compared to the reference potential of the reference electrode 42 at the standard time. Therefore, the deviation $\Delta V2$ of the voltage V2 can be either positive or negative.

Then, the diagnosing part 94 corrects the deviation of the reference potential of the reference electrode 42 based on the deviation $\Delta V2$ of the voltage V2 (step S14).

Then, the diagnosing part 94 allows the driving control part 92 to restart the normal control (step S15). Then, the diagnosis and correction processing is completed.

The diagnostic voltage current curve obtained in step S12 as a diagnostic correspondence relationship may be almost all or part of the regions of or a single point on the diagnostic voltage current curve shown in FIG. 5 as an example. For example, the diagnosing part 94 may obtain a diagnostic voltage current curve in which the electromotive force V2 or the pump current Ip2 is within a predetermined range. The obtained diagnostic voltage current curve does not need to contain all the above-described ohmic region, limiting current region, and $H_2O$ decomposition region, and part of the regions of the voltage current curve may be obtained. Alternatively, a predetermined single point on the voltage current curve may be obtained.

For example, a deviation of the reference potential of the reference electrode 42 may be diagnosed using a voltage V2(ohmic) at which the pump current Ip2 is at a predetermined current value in the ohmic region of the voltage current curve. That is, the storing part 93 may store in advance, as the standard correspondence relationship, a standard voltage V2(ohmic)a between the measurement electrode 44 and the reference electrode 42 when the pump current Ip2 is at a predetermined current value in the ohmic region in which the relationship of the pump current Ip2 flowing through the measurement pump cell 41 and the voltage V2 between the measurement electrode 44 and the reference electrode 42 is linear, at a standard time at which the reference potential of the reference electrode 42 is at a predetermined value, and the diagnosing part 94 may obtain in step S12, as the diagnostic correspondence relationship, a diagnostic voltage V2(ohmic)b between the measurement electrode 44 and the reference electrode 42 when the pump current Ip2 is at the predetermined current value, and may compare in step S13, the obtained diagnostic voltage V2(ohmic)b with the standard voltage V2(ohmic)a stored in advance in the storing part 93 to diagnose a deviation of the reference potential of the reference electrode 42 at the diagnostic time from the predetermined value at the standard time. In this case, a deviation of the diagnostic voltage V2(ohmic)b from the standard voltage V2(ohmic)a, ΔV2 (ohmic) (=V2 (ohmic)b−V2(ohmic)a) almost corresponds to a deviation of the reference potential of the reference electrode 42.

It is noted that the predetermined current value of the pump current Ip2 may either be a positive value or a negative value as long as it falls within the range of the ohmic region. That is, the predetermined current value of the pump current Ip2 may be in either a positive direction for pumping out oxygen from the surroundings of the measurement electrode 44 or a negative direction for pumping oxygen into the surroundings of the measurement electrode 44. Alternatively, for example, the predetermined current value of the pump current Ip2 may be zero or a value around zero.

Alternatively, for example, a deviation of the reference potential of the reference electrode 42 may be diagnosed using a voltage V2($H_2O$) at a start point of the $H_2O$ decomposition region of the voltage current curve or a point around it. That is, the storing part 93 may store in advance, as the standard correspondence relationship, a standard voltage V2($H_2O$)a between the measurement electrode 44 and the reference electrode 42 when water ($H_2O$) starts to be decomposed in the measurement electrode 44, at a standard time at which the reference potential of the reference electrode 42 is at a predetermined value, and the diagnosing part 94 may obtain in step S12, as the diagnostic correspondence relationship, a diagnostic voltage V2($H_2O$)b between the measurement electrode 44 and the reference electrode 42 when water ($H_2O$) starts to be decomposed in the measurement electrode 44, and may compare in step S13, the obtained diagnostic voltage V2($H_2O$)b with the standard voltage V2($H_2O$)a stored in advance in the storing part 93 to diagnose a deviation of the reference potential of the reference electrode 42 at the diagnostic time from the predetermined value at the standard time. In this case, a deviation of the diagnostic voltage V2($H_2O$)b from the standard voltage V2($H_2O$)a, ΔV2($H_2O$) (=V2($H_2O$) b−V2($H_2O$)a) almost corresponds to a deviation of the reference potential of the reference electrode 42. For example, an inflection point between the limiting current region and the $H_2O$ decomposition region in the voltage current curve may be defined as a water ($H_2O$) decomposition start point, or a point at which the rate of change of the pump current Ip2 with respect to the voltage V2 is equal to or larger than a predetermined value may be defined as a water ($H_2O$) decomposition start point. The time at which the voltage V2($H_2O$) is obtained is not limited to the time at which water ($H_2O$) starts to be decomposed in the measurement electrode 44, and the diagnosis may be performed using a voltage V2($H_2O$) obtained when a predetermined amount/ratio of $H_2O$ is decomposed.

Alternatively, for example, a deviation of the reference potential of the reference electrode 42 may be diagnosed using a voltage V2(limit) at a start point of the limiting current region of the voltage current curve or a point around it. That is, the storing part 93 may store in advance, as the standard correspondence relationship, a standard voltage V2(limit)a when the pump current Ip2 flowing through the measurement pump cell 41 reaches a limiting current (at a start point of the limiting current region), at a standard time at which the reference potential of the reference electrode 42 is at a predetermined value, and the diagnosing part 94 may obtain in step S12, as the diagnostic correspondence relationship, a diagnostic voltage V2(limit)b between the measurement electrode 44 and the reference electrode 42 when the pump current Ip2 flowing through the measurement pump cell 41 reaches a limiting current, and may compare in step S13, the obtained diagnostic voltage V2(limit)b with the standard voltage V2(limit)a stored in advance in the storing part 93 to diagnose a deviation of the reference potential of the reference electrode 42 at the diagnostic time from the predetermined value at the standard time. In this case, a deviation of the diagnostic voltage V2(limit)b from the standard voltage V2(limit)a, ΔV2 (limit) (=V2(limit)b−V2(limit)a) almost corresponds to a deviation of the reference potential of the reference electrode 42. For example, an inflection point between the ohmic region and the limiting current region in the voltage current curve may be defined as a start point of the limiting current region, or a point at which the rate of change of the pump current Ip2 with respect to the voltage V2 is equal to or less than a predetermined value may be defined as a start point of the limiting current region.

When the above-described diagnostic voltage V2(ohmic) b, V2($H_2O$)b, or V2(limit)b is used as a diagnostic correspondence relationship, the amount of time required for step S11 can be reduced as compared to when the entirety of the voltage current curve is used because the sweeping range of the pump voltage Vp2 can be reduced or a diagnostic voltage can be obtained simply by applying a predetermined voltage without sweeping the pump voltage Vp2 in step S11. As a result, the diagnosis and correction processing can be completed in a shorter time, and therefore a time period when the NOx concentration in a measurement-object gas is not measured during the use of the gas sensor 100 can further be reduced. Further, the ohmic region is less likely to be affected by deterioration of the measurement electrode 44 even when the measurement electrode 44 deteriorates due to the use of the gas sensor 100. Therefore, when a voltage V2(ohmic) at which the pump current Ip2 is at a predetermined current value in the ohmic region of the voltage current curve is used, a deviation of the reference potential of the reference electrode 42 can more accurately be diagnosed.

Figure 7:
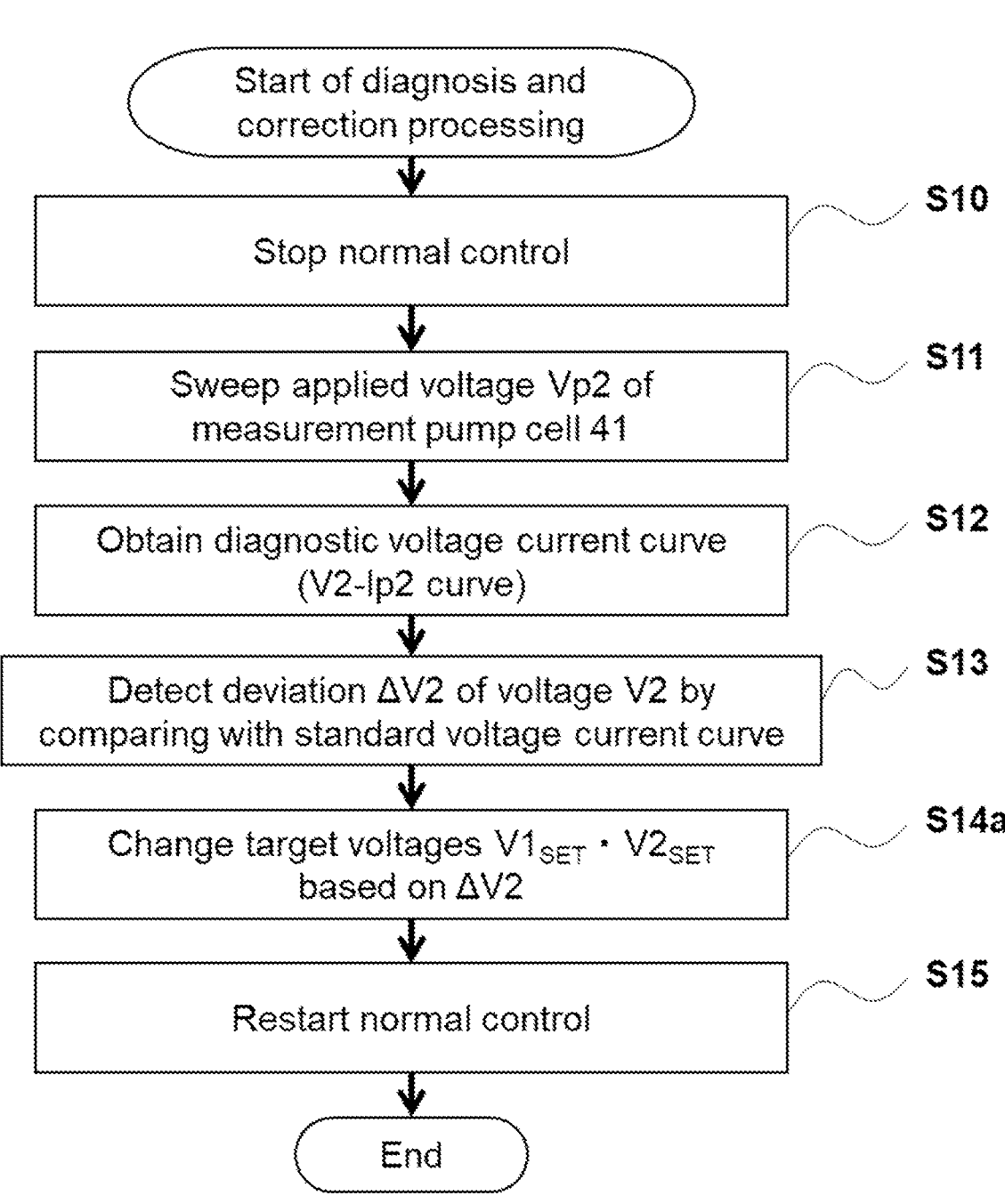
FIG. 7 is a flowchart showing a specific example of a diagnosis and correction processing.

FIG. 7 is a flow chart of the diagnosis and correction processing, which shows a specific example of correction of a deviation of the reference potential of the reference electrode 42. In FIG. 7, the same step numbers as in FIG. 6 denote the same steps, and therefore the description thereof will not be repeated.

As shown in FIG. 7, for example, the diagnosing part 94 may change the target voltage (set value V2$_{SET}$) in the normal control based on the deviation of the reference potential of the reference electrode 42 at the diagnostic time from the predetermined value at the standard time to correct the deviation from the predetermined value.

In this case, the diagnosing part 94 changes the target voltage (set value V2$_{SET}$) of the measurement pump cell 41 in the normal control based on the deviation ΔV2 of the voltage V2 calculated in step S13, that is, the deviation of the reference potential of the reference electrode 42 (step S14a). As described above, the deviation ΔV2 of the voltage V2 almost corresponds to the deviation of the reference potential of the reference electrode 42. Therefore, in step S14a, the diagnosing part 94 may further change the target voltage (set value $V1_{SET}$) of the auxiliary pump cell 50 in the normal control. For example, when the diagnostic voltage current curve shifts to the right of the standard voltage current curve as shown in FIG. 5, the target voltage (set value $V2_{SET}$ and/or set value $V1_{SET}$) may be changed to a value larger than the target voltage at the standard time. When the diagnostic voltage current curve shifts to the left of the standard voltage current curve, the target voltage (set value $V2_{SET}$ and/or set value $V1_{SET}$) may be changed to a value smaller than the target voltage at the standard time. Alternatively, for example, when the deviation of the reference potential of the reference electrode 42 is within a predetermined range that does not affect the detection accuracy of the NOx concentration, the target voltage before the diagnosis and correction processing may be maintained without changing the target voltage (set value $V2_{SET}$ and/or set value $V1_{SET}$).

Figure 8:
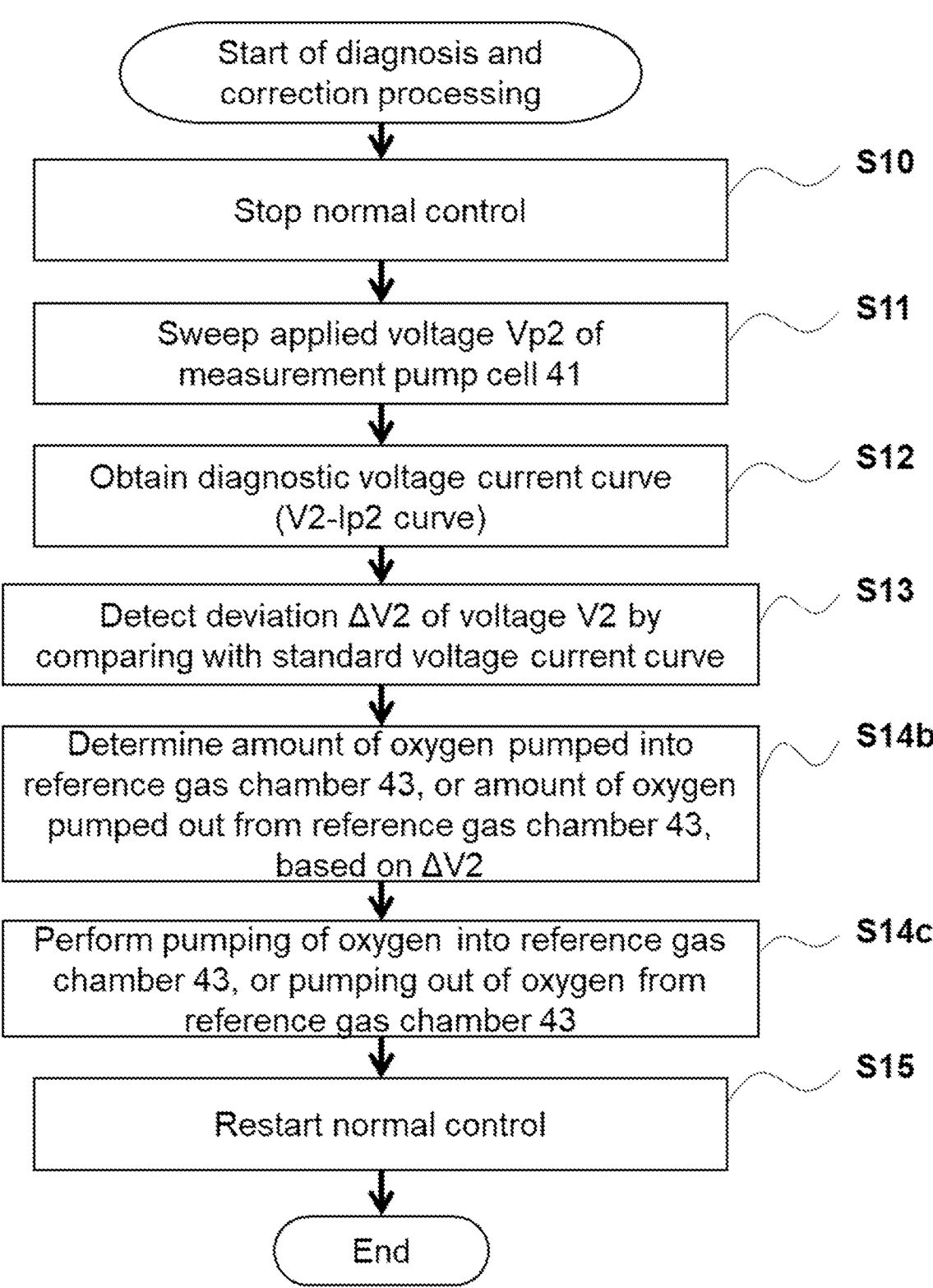
FIG. 8 is a flowchart showing another specific example of a diagnosis and correction processing.

FIG. 8 is a flow chart of the diagnosis and correction processing, which shows a specific example different from the correction of a deviation of the reference potential of the reference electrode 42 shown in FIG. 7. In FIG. 8, the same step numbers as in FIG. 6 denote the same steps as in the case of FIG. 7, and therefore the description thereof will not be repeated.

As shown in FIG. 8, for example, the diagnosing part 94 may pump oxygen into the reference gas chamber 43 or pump out oxygen from the reference gas chamber 43 based on the deviation of the reference potential of the reference electrode 42 at the diagnostic time from the predetermined value at the standard time to correct the deviation from the predetermined value.

In this case, the diagnosing part 94 determines the amount of oxygen pumped into the reference gas chamber 43 or the amount of oxygen pumped out from the reference gas chamber 43 based on the deviation $\Delta V2$ of the voltage $V2$ calculated in step S13, that is, the deviation of the reference potential of the reference electrode 42 (step S14b). For example, when the diagnostic voltage current curve shifts to the right of the standard voltage current curve as shown in FIG. 5, the reference potential of the reference electrode 42 at the diagnostic time is considered to be higher than the predetermined value at the standard time. That is, the oxygen concentration in a reference gas at the diagnostic time is considered to be higher than that at the standard time. Therefore, the correction may be performed by pumping out oxygen from the reference gas chamber 43 so that the reference potential of the reference electrode 42 reduces, that is, the oxygen concentration in a reference gas reduces. When the diagnostic voltage current curve shifts to the left of the standard voltage current curve, the correction may be performed by pumping oxygen into the reference gas chamber 43 so that the reference potential of the reference electrode 42 increases, that is, the oxygen concentration in a reference gas increases.

The diagnosing part 94 pumps oxygen into the reference gas chamber 43 or pumps out oxygen from the reference gas chamber 43 based on the determined pump-in amount of oxygen or the determined pump-out amount of oxygen (step S14c). Specifically, a pump current Ip3 is applied by applying a pump voltage Vp3 to the reference gas adjustment pump cell 84 by the power supply circuit 85. Alternatively, instead of step S14c, the diagnosing part 94 may set or change the pump-in amount of oxygen of the oxygen pump-in control in the normal control or the pump-out amount of oxygen of the oxygen pump-out control in the normal control based on the determined pump-in amount of oxygen or pump-out amount of oxygen. In this case, the deviation of the reference potential of the reference electrode 42 is corrected in the normal control after the completion of the diagnosis and correction processing.

Further, alternatively, the diagnosing part 94 may perform a combination of both of the change of the target voltage (set value $V2_{SET}$ and/or set value $V1_{SET}$) and the determination of the amount of oxygen pumped out from the reference gas chamber 43/the amount of oxygen pumped into the reference gas chamber 43.

As described above, the gas sensor 100 according to the present embodiment can diagnose a deviation of the reference potential of the reference electrode 42 and if necessary correct the deviation. When a deviation of the reference potential of the reference electrode 42 is diagnosed using the correspondence relationship of a voltage with a current, such as a voltage current curve, as in the case of the above-described diagnosis and correction processing, the oxygen concentration in a measurement-object gas does not need to be known unlike the oxygen concentration confirming step in the production process described above. Therefore, a deviation of the reference potential of the reference electrode 42 can be diagnosed at any timing during the use of the gas sensor 100 also in cases other than a case where the concentration of oxygen or NOx in a measurement-object gas is known or irrespective of the concentrations of them. Further, the deviation of the reference potential of the reference electrode 42 can be corrected based on the result of the diagnosis. This makes it possible to prevent a reduction in the detection accuracy of the NOx concentration in a measurement-object gas to maintain high measurement accuracy.

The gas sensor 100 for detecting the NOx concentration in a measurement-object gas has been described above as an example of the embodiment according to the present invention, but the present invention is not limited to this embodiment. The present invention may include various gas sensors different in configuration as long as the object of the present invention is achieved, that is, as long as a reduction in the detection accuracy of a target gas to be measured in a measurement-object gas is prevented to maintain high detection accuracy.

In the above-described embodiment, all the pump controls are stopped in step S10 in the diagnosis and correction processing, but step S10 is not limited thereto. For example, the driving control part 92 may stop only the control to feed back a pump voltage Vp2 of the measurement pump cell 41 so that the voltage $V2$ is at a set value $V2_{SET}$ while continuing to perform the control to feed back a pump voltage Vp0 of the main pump cell 21 so that the voltage $V0$ is at a set value $V0_{SET}$ and the control to feed back a pump voltage Vp1 of the auxiliary pump cell 50 so that the voltage $V1$ is at a set value $V1_{SET}$.

In this case, the operations of the main pump cell 21 and the auxiliary pump cell 50 allow a measurement-object gas whose oxygen partial pressure (oxygen concentration) is maintained at a predetermined low value to reach the measurement electrode 44. Therefore, when the normal control is restarted (step S15), a gas atmosphere around the measurement electrode 44 stabilizes in a short time, which makes it possible to more quickly start accurate measurement of the NOx concentration in a measurement-object gas after the completion of the diagnosis and correction processing. Further, when the main pump cell 21 and the auxiliary pump cell 50 are operated, around the measurement electrode 44, oxygen $O_2$ is hardly present, but NOx originally present in a measurement-object gas is present.

The $O_2$ concentration in a measurement-object gas may vary in the range of 0% to about 21% (air), but on the other hand, the NOx concentration is usually considered to be about 0 to 5000 ppm. Therefore, as compared to when all the pump controls are stopped, the gas atmosphere around the measurement electrode 44 at the diagnostic time is less likely to vary from diagnosis to diagnosis and the difference thereof from that at the standard time is also smaller. Therefore, a deviation of the reference potential of the reference electrode 42 at the diagnostic time from the reference potential at the standard time can more accurately be detected.

It is noted that in a case where the diagnosing part 94 obtains a diagnostic correspondence relationship when only the control of the measurement pump cell 41 is stopped, the storing part 93 stores in advance a standard correspondence relationship at a time when only the control of the measurement pump cell 41 is stopped.

Further, in the above-described embodiment, the pump voltage Vp2 is applied to the measurement pump cell 41 and is swept within a predetermined range in step S11 of the diagnosis and correction processing, but step S11 is not limited thereto. For example, the diagnosing part 94 may obtain a V2-Ip2 curve by sweeping the pump current Ip2 within a predetermined range by a current supply to detect a voltage V2 between the measurement electrode 44 and the reference electrode 42.

Further, in the above-described embodiment, the diagnosis and correction processing is performed using the voltage current curve (V2-Ip2 curve) between the measurement electrode 44 and the reference electrode 42, but the voltage current curve used in the diagnosis and correction processing is not limited thereto. The voltage current curve to be used may be a voltage current curve (V0-Ip0 curve) between the inner main pump electrode 22 and the reference electrode 42 or a voltage current curve (V1-Ip1 curve) between the auxiliary pump electrode 51 and the reference electrode 42. It is noted that in this case, all the pump controls may be stopped as in the case of step S10 in the diagnosis and correction processing described above.

In the above-described embodiment, the reference gas chamber 43 is a space closed inside the base part 102. However, the reference gas chamber 43 is not limited thereto. For example, the reference gas chamber 43 may entirely or partially be filled with a porous material such as alumina.

Figure 9:
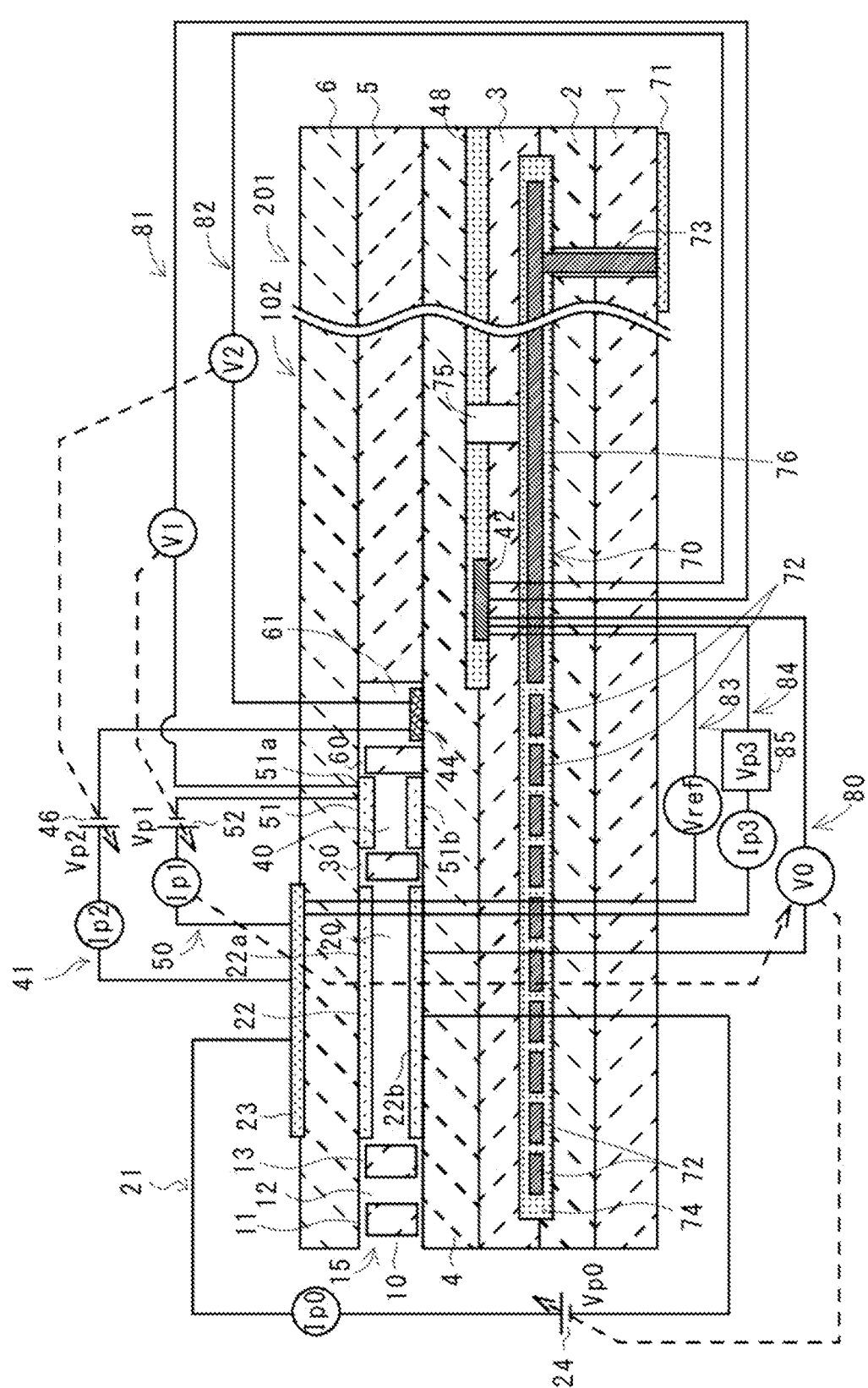
FIG. 9 is a vertical sectional schematic view in a longitudinal direction of a sensor element 201 of a Variation.

Alternatively, for example, the reference gas chamber may be formed as a porous reference gas introduction layer 48 as in the case of a sensor element 201 shown in FIG. 9. In the sensor element 201, the reference gas introduction later 48 is provided between the upper surface of the third substrate layer 3 and the lower surface of the first solid electrolyte layer 4 to cover the reference electrode 42. The reference gas introduction layer 48 is, for example, a porous body made of ceramics such as alumina. The rear end surface of the reference gas introduction layer 48 is exposed on the rear end surface of the sensor element 201. The sensor element 201 shown in FIG. 9 further includes a pressure relief vent 75. The pressure relief vent 75 is formed to extend through the third substrate layer 3 so that the heater insulating layer 74 and the reference gas introduction layer 48 as a reference gas chamber communicate with each other. The pressure relief vent 75 can mitigate an increase in internal pressure due to temperature rise in the heater insulating layer 74. The configuration of the sensor element 201 shown in FIG. 9 other than these is substantially the same as that of the sensor element 101 described with reference to FIG. 2. When the sensor element 201 is incorporated into the gas sensor 100 in the same manner as shown in FIG. 1, the rear end surface of the reference gas introduction layer 48 is exposed to the space 149 in FIG. 1 (see FIG. 1). Therefore, a reference gas is introduced into the reference gas introduction layer 48 from the space 149. In this case, the reference gas is an atmosphere gas (e.g., air) in the space 149 in FIG. 1.

Figure 10:
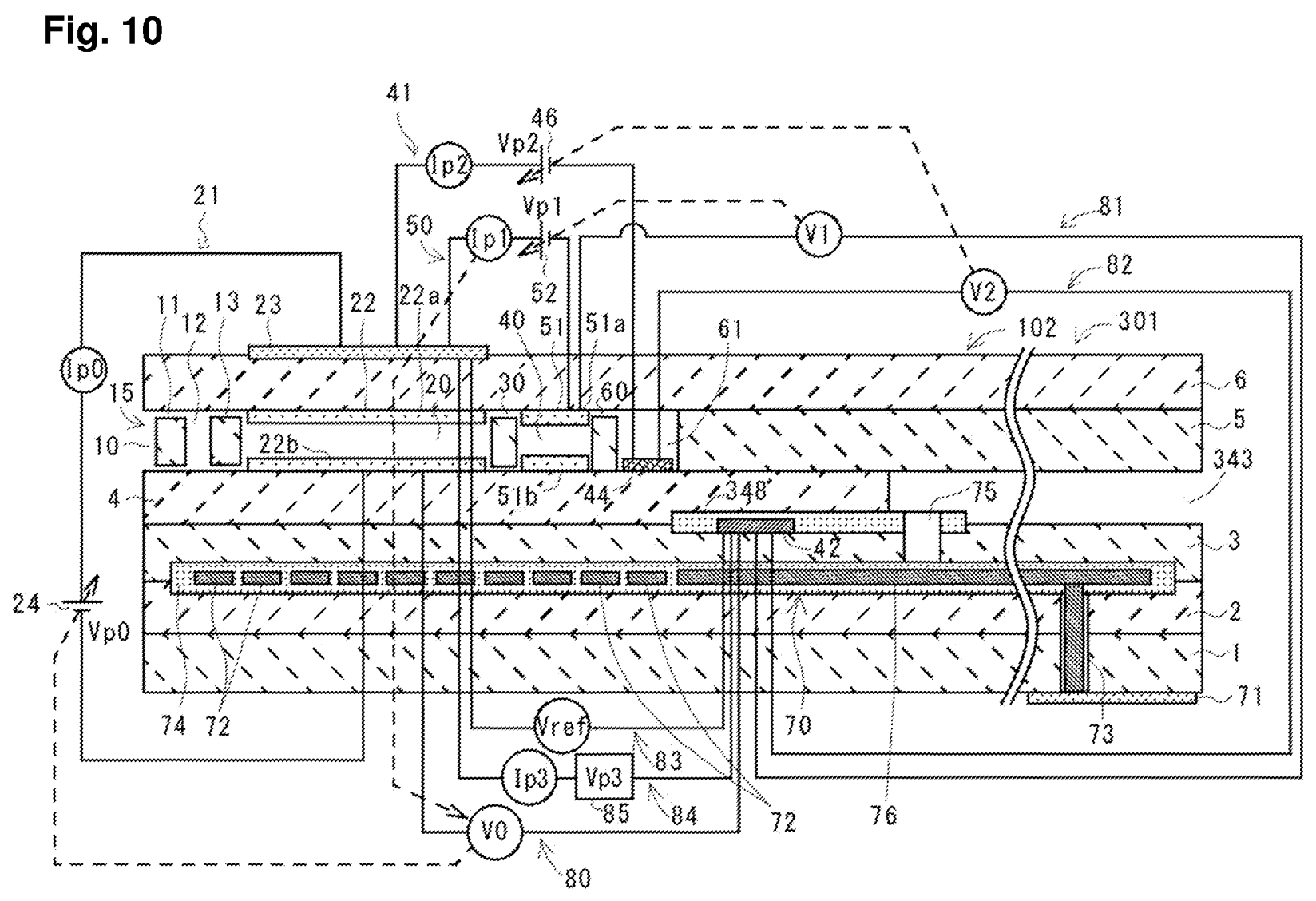

Alternatively, for example, the reference gas chamber may be formed as a space open to the rear end of the base part 102 as in the case of a sensor element 301 shown in FIG. 10. In the sensor element 301, a reference gas introduction later 348 is provided between the upper surface of the third substrate layer 3 and the lower surface of the first solid electrolyte layer 4 to cover the reference electrode 42. Further, at the rear of the reference electrode 42, a reference gas introduction space 343 is provided between the upper surface of the third substrate layer 3 and the lower surface of the spacer layer 5 at a position where the reference gas introduction space 43 is laterally defined by the lateral surface of the first solid electrolyte layer 4. The reference gas introduction space 343 has an opening at the rear end of the sensor element 301. The sensor element 301 shown in FIG. 10 further includes a pressure relief vent 75 as in the case of the sensor element 201 shown in FIG. 9. The configuration of the sensor element 301 shown in FIG. 10 other than these is substantially the same as that of the sensor element 101 described with reference to FIG. 2. When the sensor element 301 is incorporated into the gas sensor 100 in the same manner as shown in FIG. 1, the opening of the reference gas introduction space 343 is exposed to the space 149 in FIG. 1 (see FIG. 1). Therefore, a reference gas is introduced into the reference gas introduction space 343 from the space 149. In this case, the reference gas is an atmosphere gas (e.g., air) in the space 149 in FIG. 1. The reference gas introduced into the reference gas introduction space 343 reaches the reference electrode 42 through the reference gas introduction layer 348.

The sensor element 201 and the sensor element 301 have a structure such that a reference gas is introduced into the reference electrode 42 from an external space. In the case of the gas sensor including such a sensor element, when the pressure of a measurement-object gas temporarily increases, the oxygen concentration in a reference gas may reduce due to slight inflow of the measurement-object gas. Further, when the gas sensor is used in a high-temperature environment, the oxygen concentration in a reference gas may reduce as gas is generated due to erosion of the rubber plug 157 exposed to high temperature, or as oil adhering to the outer cylinder 148 reacts with oxygen due to high temperature. Even in such a case, the diagnosis and correction processing makes it possible to prevent a reduction in the detection accuracy of the NOx concentration in a measurement-object gas to maintain high measurement accuracy.

Further, in the case of the gas sensor having a structure such that a reference gas is introduced into the reference electrode 42 from an external space, an oxygen pump-in control to pump oxygen into the reference gas chamber 43 is preferably performed in the normal control by applying a pump voltage Vp3 to the reference gas adjustment pump cell 84 by the power supply circuit 85 to apply a pump current Ip3. When the oxygen pump-in control is performed, for example, the pump-in amount of oxygen of the oxygen pump-in control in the normal control may be changed based on the deviation of the reference potential of the reference electrode 42 in the diagnosis and correction processing.

Further, the sensor element 101 according to the embodiment described above may further include a pressure relief vent for mitigating an increase in internal pressure due to temperature rise in the heater insulating layer 74. In this case, unlike the pressure relief vent 75 shown in FIG. 9 and FIG. 10, the pressure relief vent may be formed so that it does not communicate with the reference gas chamber 43, but the heater insulating layer 74 and a space outside the sensor element 101 communicate with each other.

In the gas sensor 100 of the above embodiment, as shown in FIG. 2, the sensor element 101 has a structure in which three internal cavities, the first internal cavity 20, the second internal cavity 40, and the third internal cavity 61 are provided and the inner main pump electrode 22, the auxiliary pump electrode 51, and the measurement electrode 44 are respectively disposed in these internal cavities. However, the structure of the sensor element 101 is not limited thereto. For example, the sensor element 101 may have a structure in which two internal cavities, the first internal cavity 20 and the second internal cavity 40 are provided, the inner main pump electrode 22 is disposed in the first internal cavity 20, and the auxiliary pump electrode 51 and the measurement electrode 44 are disposed in the second internal cavity 40. In this case, for example, a porous protective layer covering the measurement electrode 44 may be formed as a diffusion-rate limiting part between the auxiliary pump electrode 51 and the measurement electrode 44.

In the gas sensor 100 of the above embodiment, the outer pump electrode 23 has three functions as an outer main pump electrode in the main pump cell 21, an outer auxiliary pump electrode in the auxiliary pump cell 50, and an outer measurement electrode in the measurement pump cell 41. However, the outer pump electrode 23 is not limited thereto. For example, the outer main pump electrode, the outer auxiliary pump electrode, and the outer measurement electrode may be formed as different electrodes. For example, any one or more of the outer main pump electrode, the outer auxiliary pump electrode, and the outer measurement electrode may be provided on the outer surface of the base part 102 separately from the outer pump electrode 23 so as to be in contact with a measurement-object gas. Alternatively, the reference electrode 42 may also serve as any one or more of the outer main pump electrode, the outer auxiliary pump electrode, and the outer measurement electrode. However, when the reference electrode 42 is used as any one or more of the outer main pump electrode, the outer auxiliary pump electrode, and the outer measurement electrode, the oxygen concentration in the reference gas in the reference gas chamber 43 may be changed. Therefore, it should be noted that the reference electrode 42 is used to the extent that measurement accuracy is not substantially affected.

In the above embodiment, the gas sensor 100 detects the NOx concentration in a measurement-object gas. However, the target gas to be measured is not limited to NOx. The sensor element of the gas sensor 100 may have a structure using an oxygen-ion-conductive solid electrolyte. For example, the target gas to be measured may be oxygen $O_2$, or an oxide gas other than NOx (e.g., carbon dioxide $CO_2$, water $H_2O$). Alternatively, the target gas to be measured may be a non-oxide gas such as ammonia $NH_3$. When the target gas to be measured is a non-oxide gas, the non-oxide gas is converted to an oxide gas (for example, in the case of ammonia $NH_3$, $NH_3$ is converted to NO), and a measurement-object gas containing the converted oxide gas is introduced into the third internal cavity 61. At the measurement electrode 44, the converted oxide gas in the measurement-object gas is reduced so that oxygen is generated. The target gas to be measured can be detected by acquiring the generated oxygen as the pump current Ip2 in the measurement pump cell 41. The conversion from the non-oxide gas to the oxide gas can be performed by allowing at least one of the inner main pump electrode 22 and the auxiliary pump electrode 51 to function as a catalyst.

As has been described above, according to the present invention, it is possible to diagnose a deviation of a reference potential of the reference electrode at any timing during the use of the gas sensor also in cases other than a case where the oxygen concentration in a measurement-object gas is known or irrespective of the oxygen concentration. That is, it is possible to diagnose a deviation of the oxygen concentration in a reference gas around the reference electrode. Further, it is possible to correct a deviation of a reference potential of the reference electrode, that is, a deviation of the oxygen concentration in a reference gas based on the result of the diagnosis. As a result, it is possible to prevent a reduction in the detection accuracy of the target gas to be measured to maintain high detection accuracy.

EXPLANATION OF REFERENCE SIGNS IN THE DRAWINGS

1: first substrate layer; 2: second substrate layer; 3: third substrate layer; 4: first solid electrolyte layer; 5: spacer layer; 6: second solid electrolyte layer; 10: gas inlet; 11: first diffusion-rate limiting part; 12: buffer space; 13: second diffusion-rate limiting part; 15: measurement-object gas flow cavity; 20: first internal cavity; 21: main pump cell; 22: inner main pump electrode; 22a: ceiling electrode portion (of the inner main pump electrode); 22b: bottom electrode portion (of the inner main pump electrode); 23: outer pump electrode; 24: variable power supply (of the main pump cell); 30: third diffusion-rate limiting part; 40: second internal cavity; 41: measurement pump cell; 42: reference electrode; 43: reference gas chamber; 343: reference gas introduction space; 44: measurement electrode; 46: variable power supply (of the measurement pump cell); 48, 348: reference gas introduction layer; 50: auxiliary pump cell; 51: auxiliary pump electrode; 51a: ceiling electrode portion (of the auxiliary pump electrode); 51b: bottom electrode portion (of the auxiliary pump electrode); 52: variable power supply (of the auxiliary pump cell); 60: fourth diffusion-rate limiting part; 61: third internal cavity; 70: heater part; 71: heater connector electrode; 72: heater; 73: through hole; 74: heater insulating layer; 75: pressure relief vent; 76: heater lead; 80: oxygen-partial-pressure detection sensor cell for main pump control; 81: oxygen-partial-pressure detection sensor cell for auxiliary pump control; 82: oxygen-partial-pressure detection sensor cell for measurement pump control; 83: sensor cell; 84: reference gas adjustment pump cell; 85: power supply circuit; 90: control unit; 91: control part; 92: drive control part; 93: storing part; 94: diagnosing part; 100: gas sensor; 101, 201, 301: sensor element; and 102: base part.

What is claimed is:

1. A gas sensor for detecting a target gas to be measured in a measurement-object gas, the gas sensor comprising a sensor element and a control unit for controlling the sensor element, wherein
the sensor element comprises:
a base part in an elongated plate shape, including an oxygen-ion-conductive solid electrolyte layer;
a measurement-object gas flow cavity formed from one end part in a longitudinal direction of the base part;
a pump cell including: an intracavity electrode disposed in the measurement-object gas flow cavity; and an extracavity electrode disposed at a position different from the measurement-object gas flow cavity on the base part and corresponding to the intracavity electrode;

a reference gas chamber formed inside the base part, and being separated from the measurement-object gas flow cavity; and a reference electrode disposed in the reference gas chamber, and the control unit comprises:

a driving control part operating the pump cell to perform a normal control for detecting the target gas to be measured in the measurement-object gas;

a storing part storing in advance, a standard correspondence relationship of a voltage between the intracavity electrode and the reference electrode with a current flowing through the pump cell, at a standard time at which a reference potential of the reference electrode is at a predetermined value; and a diagnosing part obtaining a diagnostic correspondence relationship of a voltage between the intracavity electrode and the reference electrode with a current flowing through the pump cell at a diagnostic time at which the reference potential of the reference electrode is diagnosed, and comparing the obtained diagnostic correspondence relationship with the standard correspondence relationship stored in advance in the storing part to diagnose a deviation of the reference potential of the reference electrode at the diagnostic time from the predetermined value at the standard time, wherein the storing part stores in advance, as the standard correspondence relationship, a standard voltage between the intracavity electrode and the reference electrode at a time at which a current flowing through the pump cell is at a predetermined current value in an ohmic region in which a relationship of the voltage between the intracavity electrode and the reference electrode with the current flowing through the pump cell is linear, at the standard time at which the reference potential of the reference electrode is at the predetermined value, and the diagnosing part obtains, as the diagnostic correspondence relationship, a diagnostic voltage between the intracavity electrode and the reference electrode at the time at which the current flowing through the pump cell is at the predetermined current value, and compares the obtained diagnostic voltage with the standard voltage stored in advance in the storing part to diagnose the deviation of the reference potential of the reference electrode at the diagnostic time from the predetermined value at the standard time.

2. The gas sensor according to claim 1, wherein the pump cell is:

a measurement pump cell including: an inner measurement electrode disposed in the measurement-object gas flow cavity; and an outer measurement electrode disposed at a position different from the measurement-object gas flow cavity on the base part and corresponding to the inner measurement electrode, the driving control part applies a current to the measurement pump cell so that a voltage between the inner measurement electrode and the reference electrode is a target voltage to measure a concentration of the target gas to be measured in the measurement-object gas based on a value of the current in the normal control, and the diagnosing part further changes the target voltage in the normal control based on the deviation of the reference potential of the reference electrode at the diagnostic time from the predetermined value at the standard time to correct the deviation from the predetermined value.

3. The gas sensor according to claim 1, wherein the diagnosing part further pumps oxygen into the reference gas chamber or pumps out oxygen from the reference gas chamber based on the deviation of the reference potential of the reference electrode at the diagnostic time from the predetermined value at the standard time to correct the deviation from the predetermined value.

4. The gas sensor according to claim 1, wherein the reference gas chamber is a space closed inside the base part.

5. A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

a pump cell including: an intracavity electrode disposed in the measurement-object gas flow cavity; and an extracavity electrode disposed at a position different from the measurement-object gas flow cavity on the base part and corresponding to the intracavity electrode;

a reference gas chamber formed inside the base part, and being separated from the measurement-object gas flow cavity; and a reference electrode disposed in the reference gas chamber, and the control unit comprises:

a driving control part operating the pump cell to perform a normal control for detecting the target gas to be measured in the measurement-object gas;

a storing part storing in advance, a standard correspondence relationship of a voltage between the intracavity electrode and the reference electrode with a current flowing through the pump cell, at a standard time at which a reference potential of the reference electrode is at a predetermined value; and a diagnosing part obtaining a diagnostic correspondence relationship of a voltage between the intracavity electrode and the reference electrode with a current flowing through the pump cell at a diagnostic time at which the reference potential of the reference electrode is diagnosed, and comparing the obtained diagnostic correspondence relationship with the standard correspondence relationship stored in advance in the storing part to diagnose a deviation of the reference potential of the reference electrode at the diagnostic time from the predetermined value at the standard time, wherein the storing part stores in advance, as the standard correspondence relationship, a standard voltage between the intracavity electrode and the reference electrode at a time at which water ($H_2O$) starts to be decomposed in the intracavity electrode, at the standard time at which the reference potential of the reference electrode is at the predetermined value, and the diagnosing part obtains, as the diagnostic correspondence relationship, a diagnostic voltage between the intracavity electrode and the reference electrode at the time at which water ($H_2O$) starts to be decomposed in the intracavity electrode, and compares the obtained diagnostic voltage with the standard voltage stored in advance in the storing part to diagnose the deviation of the reference potential of the reference electrode at the diagnostic time from the predetermined value at the standard time.

6. The gas sensor according to claim 5, wherein the pump cell is:

a measurement pump cell including: an inner measurement electrode disposed in the measurement-object gas flow cavity; and an outer measurement electrode disposed at a position different from the measurement-object gas flow cavity on the base part and corresponding to the inner measurement electrode, the driving control part applies a current to the measurement pump cell so that a voltage between the inner measurement electrode and the reference electrode is a target voltage to measure a concentration of the target gas to be measured in the measurement-object gas based on a value of the current in the normal control, and the diagnosing part further changes the target voltage in the normal control based on the deviation of the reference potential of the reference electrode at the diagnostic time from the predetermined value at the standard time to correct the deviation from the predetermined value.

7. The gas sensor according to claim 5, wherein the diagnosing part further pumps oxygen into the reference gas chamber or pumps out oxygen from the reference gas chamber based on the deviation of the reference potential of the reference electrode at the diagnostic time from the predetermined value at the standard time to correct the deviation from the predetermined value.

8. The gas sensor according to claim 5, wherein the reference gas chamber is a space closed inside the base part.

9. A gas sensor for detecting a target gas to be measured in a measurement-object gas, the gas sensor comprising a sensor element and a control unit for controlling the sensor element, wherein the sensor element comprises:

a base part in an elongated plate shape, including an oxygen-ion-conductive solid electrolyte layer;

a measurement-object gas flow cavity formed from one end part in a longitudinal direction of the base part;

a pump cell including: an intracavity electrode disposed in the measurement-object gas flow cavity; and an extracavity electrode disposed at a position different from the measurement-object gas flow cavity on the base part and corresponding to the intracavity electrode;

a reference gas chamber formed inside the base part, and being separated from the measurement-object gas flow cavity; and a reference electrode disposed in the reference gas chamber, and the control unit comprises:

a driving control part operating the pump cell to perform a normal control for detecting the target gas to be measured in the measurement-object gas;

a storing part storing in advance, a standard correspondence relationship of a voltage between the intracavity electrode and the reference electrode with a current flowing through the pump cell, at a standard time at which a reference potential of the reference electrode is at a predetermined value; and a diagnosing part obtaining a diagnostic correspondence relationship of a voltage between the intracavity electrode and the reference electrode with a current flowing through the pump cell at a diagnostic time at which the reference potential of the reference electrode is diagnosed, and comparing the obtained diagnostic correspondence relationship with the standard correspondence relationship stored in advance in the storing part to diagnose a deviation of the reference potential of the reference electrode at the diagnostic time from the predetermined value at the standard time, wherein the storing part stores in advance, as the standard correspondence relationship, a standard voltage between the intracavity electrode and the reference electrode at a time at which a current flowing through the pump cell first reaches a limiting current, and the diagnosing part obtains, as the diagnostic correspondence relationship, a diagnostic voltage between the intracavity electrode and the reference electrode at the time at which the current flowing through the pump cell first reaches the limiting current, and compares the obtained diagnostic voltage with the standard voltage stored in advance in the storing part to diagnose the deviation of the reference potential of the reference electrode at the diagnostic time from the predetermined value at the standard time.

10. The gas sensor according to claim 9, wherein the pump cell is:

a measurement pump cell including: an inner measurement electrode disposed in the measurement-object gas flow cavity; and an outer measurement electrode disposed at a position different from the measurement-object gas flow cavity on the base part and corresponding to the inner measurement electrode, the driving control part applies a current to the measurement pump cell so that a voltage between the inner measurement electrode and the reference electrode is a target voltage to measure a concentration of the target gas to be measured in the measurement-object gas based on a value of the current in the normal control, and the diagnosing part further changes the target voltage in the normal control based on the deviation of the reference potential of the reference electrode at the diagnostic time from the predetermined value at the standard time to correct the deviation from the predetermined value.

11. The gas sensor according to claim 9, wherein the diagnosing part further pumps oxygen into the reference gas chamber or pumps out oxygen from the reference gas chamber based on the deviation of the reference potential of the reference electrode at the diagnostic time from the predetermined value at the standard time to correct the deviation from the predetermined value.

12. The gas sensor according to claim 9, wherein the reference gas chamber is a space closed inside the base part.

* * * * *